United States Patent [19]

Taylor et al.

[11] Patent Number: 5,206,701
[45] Date of Patent: Apr. 27, 1993

[54] APPARATUS FOR NEAR-INFRARED SPECTROPHOTOMETRIC ANALYSIS

[75] Inventors: James L. Taylor, Naperville; Ronald L. Cutshall, Mokena; Ernest H. Baughman, Naperville, all of Ill.

[73] Assignee: Amoco Corporation, Chicago, Ill.

[21] Appl. No.: 764,146

[22] Filed: Sep. 20, 1991

[51] Int. Cl.$^5$ .............................. G01J 3/08; G01J 3/36; G01N 21/35
[52] U.S. Cl. ................................... 356/325; 250/339; 356/328
[58] Field of Search ............... 356/319, 323, 325, 328; 250/339, 343, 353

[56] References Cited

U.S. PATENT DOCUMENTS

| | | | |
|---|---|---|---|
| 3,697,185 | 10/1972 | Kassel et al. | 356/410 |
| 3,795,805 | 3/1974 | Swanberg et al. | 250/226 X |
| 4,487,504 | 12/1984 | Goldsmith | 356/323 |
| 4,709,989 | 12/1987 | Machler | 356/328 X |
| 4,755,054 | 7/1988 | Ferree | 356/418 |
| 4,786,171 | 11/1988 | LeFebre et al. | 356/326 |
| 4,820,045 | 4/1989 | Boisde et al. | 356/319 |
| 4,836,642 | 6/1989 | Matsumoto et al. | 356/73.1 |
| 4,922,309 | 5/1990 | Sekiwa et al. | 356/328 X |
| 4,932,779 | 6/1990 | Keane | 356/323 X |
| 5,087,122 | 2/1992 | Ostrander et al. | 356/73.1 |

FOREIGN PATENT DOCUMENTS

| | | | |
|---|---|---|---|
| 56-22404 | 3/1981 | Japan | 356/73.1 |
| 60-207019 | 10/1985 | Japan | 356/319 |
| 2-293647 | 12/1990 | Japan | 356/300 |

Primary Examiner—Vincent P. McGraw
Attorney, Agent, or Firm—Thomas A. Yassen; Richard A. Kretchmer; Frank J. Sroka

[57] ABSTRACT

An apparatus is provided for obtaining spectral information and quantifying the physical properties of a sample. The apparatus comprises a light source and a high-efficiency fiber optic switch means communicating with the light source for directing the light alternatively along at least two channels, the two channels comprising at least one reference channel and at least one sample channel. A sample means communicates with the sample channel for providing an interface between the light and the sample. A fiber optic means comprising a high-efficiency fiber optic switch and/or an optical coupler communicates with the sample channels and the reference channels and directs the light alternatively from the reference and sample channels to a mode scrambler. A wavelength discrimination device separates the light from the mode scrambler into component wavelengths and provides spectral information for the determination of the physical properties of the sample. The apparatus of the present invention provides superior chemometric prediction accuracy, is reliable, durable, and stable over time, and provides outstanding performance in a manufacturing or field environment.

35 Claims, 2 Drawing Sheets

FIG. 2
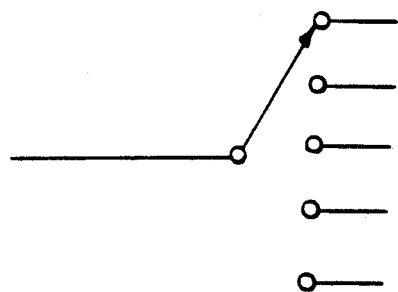
FIG. 3A     FIG. 3B
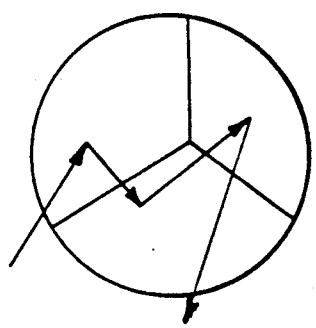 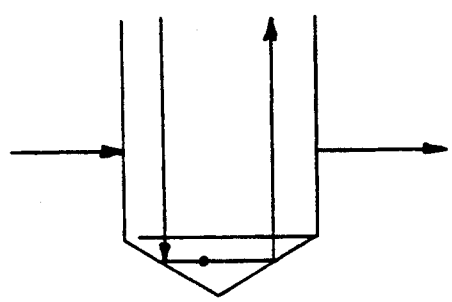
FIG. 4
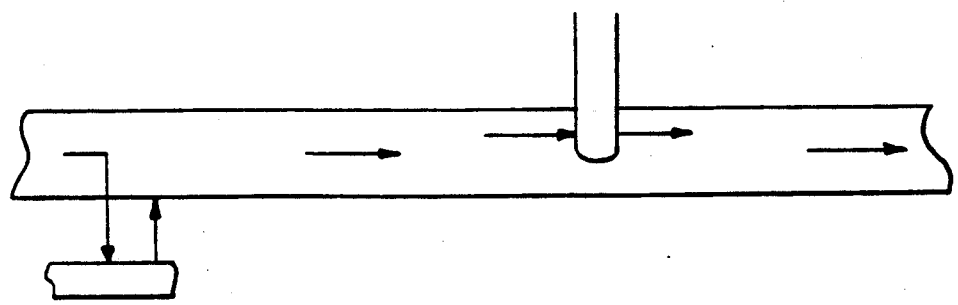

APPARATUS FOR NEAR-INFRARED SPECTROPHOTOMETRIC ANALYSIS

BACKGROUND OF THE INVENTION

This invention relates to an improved apparatus for deriving spectral information and quantifying the physical properties of a sample. More particularly, this invention relates to an improved near infrared spectrophotometer apparatus, particularly suited for determining the physical properties of a sample in an industrial environment.

The physical properties of sample materials which, for purposes of the present invention encompass the physical, chemical, and fuel properties of sample materials, have historically been measured one property at a time, utilizing test methods which have been developed to specifically evaluate one particular property. For example, the heat of formation of a particular sample has been determined by actually burning the sample in a calorimeter. Similarly, the molecular weight of a sample has been determined by inducing and measuring viscous flow of the sample using a viscometer. In each of these examples, however, the physical test methods measure, or quantify, the physical properties by actually subjecting the sample to the conditions in question. To measure more than one physical property of a particular sample, a plurality of tests must be individually conducted on a plurality of samples. Often these samples are destroyed or consumed in the process. These approaches to measuring physical properties are slow, expensive, subject to testing inconsistency, and do not facilitate on-line or real time use in an industrial or field setting.

More recently, spectrophotometric analysis has been used to determine indirectly the quantitative properties of sample materials.

U.S. Pat. No. 4,800,279 to Hieftje et al. discloses a method for utilizing near-infrared absorbance spectra to identify the physical properties of gaseous, liquid, or solid samples. The method requires measuring and recording the near-infrared absorbance spectra of a representative set of calibration samples and employing a row-reduction algorithm to determine which wavelengths in the near-infrared spectrum are statistically correlated to the physical property being quantified and to calculate weighting constants which relate the absorbance at each wavelength to the physical property being monitored. The near-infrared absorbance of a sample can then be measured at each of the correlated wavelengths and multiplied by the corresponding weighting constant. The physical property being quantified is then computed from the sum of the products of the absorbance of the sample and the corresponding weighting constant at the correlated wavelengths.

Use of spectrophotometric analysis has numerous advantages over other methods since it is rapid, relatively inexpensive, and multivariate in that many wavelengths can be measured and therefore many properties can be monitored simultaneously. While the potential for spectrophotometric analysis in manufacturing facilities, chemical plants, petroleum refineries, and the like is great, several obstacles must be overcome in order to achieve successful implementation from a practical viewpoint. These obstacles include development of an apparatus that is field durable, accurate, and stable over time under generally adverse conditions.

Most spectrophotometers typically include a light source, a grating for dispersing light in a series of monochromatic, single wavelength beams, and a suitable photodetector. The grating may be positioned to provide predispersed monochromatic light to both the sample and then the detector or, alternatively, polychromatic light from the source may be directed onto the sample and then post-dispersed by the grating before being directed to the detector. Post-dispersion permits analysis of several wavelengths simultaneously.

Several U.S. Patents have illustrated the problems and progress made towards development of a field rugged, accurate, and stable spectrophotometric device, each meeting with varying degrees of success.

One method of improving the photometric precision of prior art spectrophotometers was to provide a stable light source for illuminating the sample under analysis. For example, U.S. Pat. No. 4,094,609 teaches a means for enhancing the consistency and uniformity of the light output from the source used to irradiate the sample. However, even the best methods of providing a stable light source generally yield discernible variations in light intensity at the wavelengths of interest.

A subsequent improvement in photometric precision was made with the addition of a reference spectral pattern which could be used analytically to account for variations in the light intensity of the sample spectral pattern which were not attributable to light interaction with the sample. Spectrophotometers having a sample and reference channel are referred to as dual-channel spectrophotometers. U.S. Pat. Nos. 4,820,045 to Boisde et al., 4,932,779 to Keane, and 4,755,054 to Ferree teach use of fiber optic bundles, having multiple strands of fiber optic cable with one or more strands dedicated exclusively for providing a reference spectrum. It was subsequently found, however, that each particular fiber in the fiber optic bundle, sampled a different location on the filament of the light source and launched their respective transmitted light to different locations in the spectrophotometer. Small differences in the launching of light into and out of the fiber optics created discernible artifacts in the measured sample and reference spectra. Minor variations caused by filament vibration, small differences in intensity and color temperature along the length of the filament, inhomogeneity in the optics, and other phenomena induce different changes in the sample and reference spectra, which introduced substantial errors in quantifying the spectra. Moreover, spectrophotometric devices having fiber optic bundles generally need to be recalibrated and the chemometric model rebuilt for even the most trivial of maintenance tasks such as the routine replacement of the light source. This model rebuilding step can require the collection and the analysis of from 20 to 100 representative samples prior to proceeding with chemometric model rebuilding. These activities are costly and time consuming. Furthermore, fiber optic bundles are also substantially more costly than single fiber optic strands.

Many of the inherent problems with fiber optic bundles were addressed with the use of single strand fiber optic cable and means to launch the light alternatively to and from the sample and reference channels through the same fiber optic strand. The various means for alternatively directing light to the sample and reference channels are described in several U.S. patents.

U.S. Pat. No. 4,938,555 to Savage teaches the use of a single fiber optic strand having a moving mirror-type fiber optic light diverting means for directing light from a single fiber to one of a plurality of selected locations. Moving mirror-type fiber optic light-diverting devices generally present a number of obstacles to constructing and utilizing such a device, particularly in a manufacturing environment. The moving-mirror fiber optic diverting devices require that the light launching fibers be precisely aligned with each receiving fiber. This is particularly difficult and requires several critical multi-dimensional alignments of the optical components. These critical alignments are also particularly vulnerable to vibrationally-induced misalignment, a common concern in a field or manufacturing environment. These critical alignments are also subject to wear in the mechanical devices used to drive the mirror and select among the multiple ports of the diverting mechanism.

Moreover, the efficiency of transmitting light power from the light launching to receiving fibers is inherently low in such light-diverting devices As described in U.S. Pat. No. 4,820,045 to Boisde et al., "apart from the transmission loss due to the actual fibre, there are certain light energy loss causes at the junctions of the fibres, (particularly in collimating lenses and also during reflections at the intake of the fibres)."

Another fiber optic light-diverting means employs the use of a chopper or shutter to selectively launch light from a single fiber to a plurality of receiving ports. An example of such a light-diverting means is disclosed in U.S. Pat. No. 4,755,054 to Ferree wherein a rotatable chopper means is used to direct light from a plurality of light sources to a receiving fiber. While the chopper and shutter devices reduce the need for a critical moving optical component, chopper and shutter devices transmit light power from the light launching to receiving fibers at a particularly low efficiency. The light efficiencies inherent to these devices can be, and are generally lower than 50% of the light power introduced into the launching fiber.

Another limitation attendant to many previously disclosed spectrophotometric devices is in the means used to resolve and measure light at the various and particular wavelengths. For example, in international Application published under the Patent Cooperation Treaty WO 90/07697 to Lefebre, wavelength resolution is achieved using a moving grating monochromator. The moving grating monochromator comprises a diffraction grating rotating about a central axis relative to the light source for alternately projecting light from each narrow wavelength band onto the fiber optics leading to the sample and reference channels and subsequently to the detector. The precision and reliability of the device is limited by the repeatability of the mechanical motion of the diffraction grating. Wear on the mechanical components used to produce the motion, such as bearings, ultimately limits the wavelength precision of spectrophotometers of this design and eventually necessitates recalibration of the analyzer and development of a new chemometric model.

Alternative monochromator means have been developed to correct some of the deficiencies associated with monochromators having a moving diffraction grating. For example, some previous spectrophotometers have employed various types of filters rather than diffraction gratings for wavelength resolution. U.S. Pat. No. 4,883,963 to Kemeny et al., teaches the use of an acous-to-optical tunable filter (AOTF) for single wavelength resolution. While an AOTF obviates the need for a critical mechanical motion device in the monochromator, these devices share a common limitation with moving diffraction grating monochromators in that each wavelength in the spectrum must be analyzed sequentially and cannot be analyzed simultaneously. This limits the speed with which the spectrum can be measured and increases the cycle time for providing determinations from the analyzer. Moreover, the sequential scanning of the wavelengths can introduce artifacts and irreproducibilities, particularly in a field environment when, for example, gas bubbles appear in the sample or the sample composition changes abruptly.

We have now found that many of the previously disclosed fiber optic bundle and light diverting devices introduce artifacts into the spectrum which degrade the accuracy and precision of the analysis. These artifacts can occur from the imprecise or irreproducible imaging of light from the launching into the receiving fiber optics and generally appear as irreproducibilities in the measured spectrum. Relatively small misalignments in the imaging can result in significant irreproducibilities in the measured spectrum, with these irreproducibilities being particularly significant when the spectrophotometer is used to determine the physical properties of samples. While these irreproducibilities may be less likely to occur in a controlled laboratory environment, they are assured in an industrial facility where on-line analysis can place an analyzer under particularly harsh conditions.

We have found that the use of a mode scrambler, particularly in spectrophotometers using single fiber optic strands for the transmission of light to and from the sample, mitigates many of the effects caused by irreproducible imaging and small misalignments, which significantly improves the precision of spectral measurements. These irreproducibilities and misalignments cause unpredictable and non-uniform changes in the angular distribution of light launched from the fiber optic strand into the wavelength resolving device of the spectrophotometer. By scrambling or redistributing the modes of light propagation in the fiber optic strand, the mode scrambler gives a uniform and reproducible image of the light from the fiber optic strand into the wavelength resolving device of the spectrophotometer, which is essential for obtaining precise spectral measurements.

We have also found that the use of high efficiency fiber optic switches in tandem with a mode scrambling device to reproducibly and uniformly image light into the spectrophotometer, provides a substantial improvement in chemometric prediction precision. It has similarly been found that the addition of a spectrophotometer having a fixed diffraction grating, a single fiber optic strand for launching light from the sample and reference channels into the spectrophotometer, and an array of photodetectors for measuring the light intensity at multiple wavelength simultaneously, provides a substantial and further improvement in chemometric prediction precision, speed of analysis, and instrument versatility.

It is therefore an object of the present invention to provide an apparatus for chemometric prediction with superior chemometric prediction accuracy, reliability, durability, and stability over time, suitable for use in a manufacturing or field environment.

It is another object of the present invention to provide an apparatus for chemometric prediction without the inherent cost and inaccuracies of fiber optic bundles.

It is another object of the present invention to provide an apparatus for chemometric prediction that efficiently and precisely measures the light transmitted through the sample and reference channels of the analyzer with desensitized fiber optic switches and without other diverting devices that rely on the precise mechanical alignment of a critical optical component.

It is another object of the present invention to provide an apparatus for chemometric prediction that precisely, reproducibly, and expeditiously measures absorbances at all relevant wavelengths and is not limited to sequential wavelength measurement.

Other objects appear herein.

SUMMARY OF THE INVENTION

The above objects can be achieved by providing an apparatus for obtaining spectral information and quantifying the physical properties of a sample in accordance with the present invention. The apparatus comprises a light source and a high-efficiency fiber optic switch means communicating with the light source for directing the light alternatively along at least two channels, the two channels comprising at least one reference channel and at least one sample channel. A sample means communicates with the sample channel for providing an interface between the light and the sample. A high-efficiency fiber optic means comprising a fiber optic switch or an optical coupler communicates with the sample channels and the reference channels and directs the light alternatively from the reference and sample channels to a mode scrambler. A wavelength discrimination device separates the light from the mode scrambler into component wavelengths and provides spectral information for the determination of the physical properties of the sample.

The present invention provides an apparatus for obtaining spectral information and quantifying the physical properties of a sample that achieves superior chemometric prediction precision and is particularly reliable, durable and stable over time. An apparatus in accordance with the principals of the present invention can generally achieve a prediction accuracy for measuring composition of better than plus or minus 1.0%, better than plus or minus 0.5%, better than plus or minus 0.2%, and even consistently better than 0.1%. The apparatus utilizes substantially no moving optical components other than the high efficiency optical switches and is designed to factor out, substantially reduce, or mitigate imprecision in chemometric predictions generally incurred by prior art devices. When repairs are necessary, such as the routine replacement of the light source or repairs requiring movement of the apparatus or fiber optics, the apparatus is designed to accommodate many of these repairs without requiring recalibration of the instrument or redevelopment of the chemometric model.

The present invention provides an apparatus for obtaining spectral information and quantifying the physical properties of a sample that does not utilize fiber optic bundles or incur the inherent costs and inaccuracies of fiber optic bundles. By eliminating use of fiber optic bundles, discernable artifacts, caused by small differences in the launching of light into and out of each fiber strand in the fiber optic bundle are eliminated. Elimination of fiber optic bundles further reduces the errors in quantifying the physical properties from spectra which are induced by these artifacts and changes in these artifacts over time, and reduces the need to recalibrate and redevelop the chemometric model upon routine maintenance of the analyzer. Moreover, fiber optic bundles can cost from 10 to 100 times more than a single fiber optic strand.

The present invention provides an apparatus for obtaining spectral information and quantifying the physical properties of a sample that efficiently and precisely measures the light transmitted through the sample and reference channels of the analyzer with desensitized high-efficiency fiber optic switches and without other diverting devices that rely on the precise mechanical alignment of a critical optical component. The apparatus of the present invention utilizes high-efficiency fiber optic switches resulting in a higher signal to noise ratio and improved photometric precision. The high-efficiency fiber optic switches also substantially reduce the time required to measure the spectrum. The benefits of the high-efficiency fiber optic switches are accommodated and complemented by a mode scrambler, which compensates for the irreproducibilities in the imaging of light across the high-efficiency switches, which can be caused by misalignments in the fibers of the high-efficiency fiber optic switches upon cycling.

The present invention provides an apparatus for obtaining spectral information and quantifying the physical properties of a sample that precisely and expeditiously resolves the light intensity at all relevant wavelengths and is not limited to the measurement of light intensity at each wavelength in sequence. The apparatus of the present invention can measure the spectrum of a sample at any or all of the relevant wavelengths of interest simultaneously, which results in a substantial increase in the speed of spectral analysis and eliminates artifacts caused by abrupt changes in the composition of the sample. Faster spectral analysis results in faster sampling cycle rates and permits the analysis of a plurality of samples using the same analyzer device.

BRIEF DESCRIPTION OF THE DRAWING

FIG. 2 is a diagram of a multiplexing embodiment of a spectrophotometric apparatus in accordance with the principles of the present invention.

FIGS. 3A and 3B are diagrams of the top and side view of a sample cell embodiment of a spectrophotometric apparatus in accordance with the principles of the present invention.

FIG. 4 is a diagram of a sample cell orientation wherein the sample is directed to the sample cell through a slip-stream in accordance with the principles of the present invention.

BRIEF DESCRIPTION OF THE INVENTION

Figure 1:
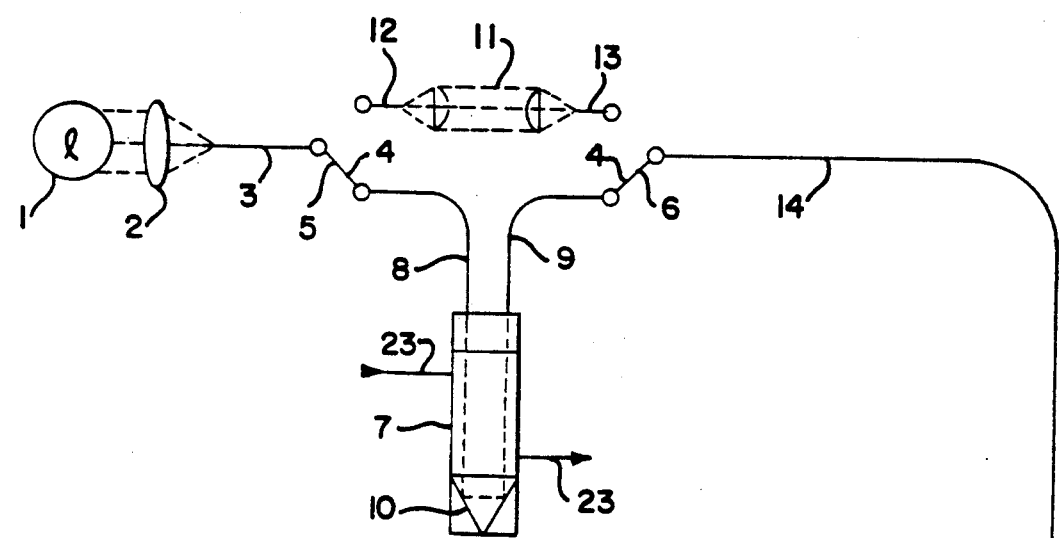
FIG. 1 is a diagram of a spectrophotometric device in accordance with the principles of the present invention.
Figure 1:
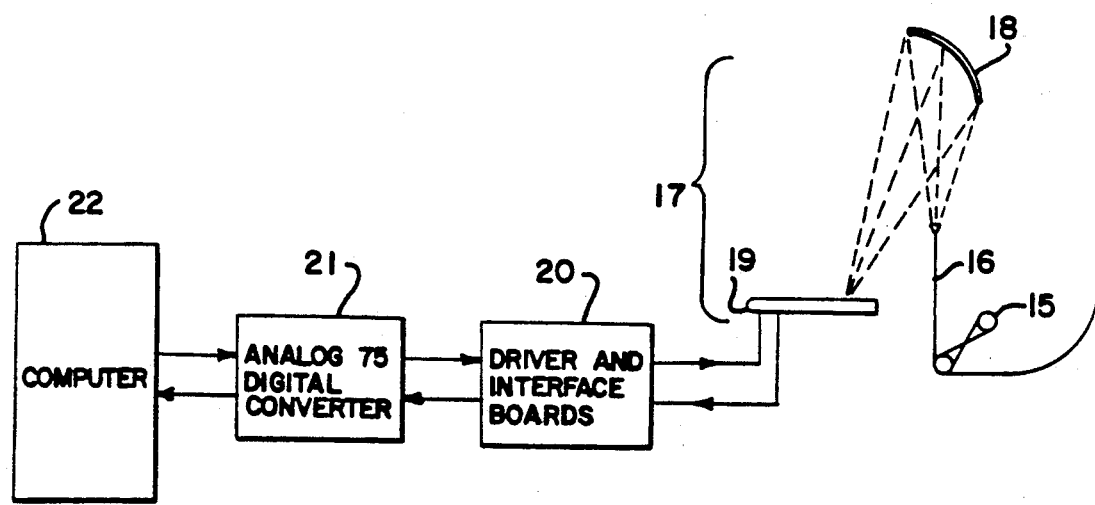

The present invention refers to an improved near infrared spectrophotometer apparatus, particularly suited for determining the physical properties of a sample in an industrial environment. For the purpose of the present invention, spectral information refers to light having wavelengths in the ultraviolet (100 nanometers to about 400 nanometers), visible (400 nanometers to about 800 nanometers), and near-infrared (800 nanometers to about 2,500 nanometers) regions. Spectral images, for purpose of the present invention, are the particular spectra or segments of spectra, often described as the relationship of optical wavelength, frequency, or the like (x-axis) and absorbance, transmittance, light intensity, or the like (y-axis), corresponding to a particular spectrophotometric analysis.

The optical features of the near-infrared range, a range particularly suited for the analysis of the physical properties of hydrocarbons, are generally combinations and overtones of vibrational modes found in the infrared region (2,500 nanometers to about 25,000 nanometers). Generally, asymmetric bonds having dipole moments create detectable and distinguishable features in the near infrared region. In particular, combinations and overtones associated with the fundamental infrared absorbance associated with the bonds H-X, where H is hydrogen and X is carbon, nitrogen, oxygen, or sulfur, give particularly intense features. Three overtone bands of the H-C stretching mode and three combination bands of C-H stretching and bending modes are found in the near infrared region. Each set of overtone and combination bands contain similar information.

Since some bands in the near-infrared range contain similar information, a narrower frequency range can be utilized to obtain accurate determinations of physical properties. Generally, any overtone band, combination band, or combination of overtone and combination bands can be utilized, however, a particular range is generally preferred depending on the system under analysis. For example, for the analysis of transparent petroleum liquid products, the wavelength range of between about 850 nanometers to about 1000 nanometers and spanning the third carbon-hydrogen stretching overtone is particularly useful because the optical path length preferred for analyzing these samples is at the convenient value of about 10–200 millimeters. Crude petroleum streams can be preferably analyzed over wavelength ranges spanning the carbon-hydrogen combination band of from about 1300 nanometers to about 1500 nanometers and the first carbon-hydrogen stretching overtone of between about 1600 nanometers to about 1800 nanometers. These higher wavelength ranges can be preferred because crude petroleum oils, unlike refined petroleum products, have several strong absorbances due to electronic transitions occurring below 1200 nanometers which interfere with and obscure the combination and overtone bands rendering the spectra below 1200 nanometers less useful for chemometric prediction.

Traditionally, spectrophotometric analysis has been used to determine the qualitative nature of compounds and complex mixtures from their spectral information. However, physical properties can also be quantitatively correlated to spectral information where the property is related to the composition or heuristically correlated to the spectra, even when the property is not obviously related to composition. Quantitative determinations are also well suited to spectrophotometric analysis, and in particular, spectrophotometric analysis utilizing near-infrared spectra. According to the Beer-Lambert law, absorbance (A) is proportional to the weight fraction of the absorbing species (W) as described in the following equations:

$$A = \text{Log}(I_o/I) = \epsilon L \rho W$$

where $I_o$ is the light intensity incident on the sample, I is the light intensity transmitted through the sample, $\epsilon$ is the absorption coefficient, L is the path length through the sample, and $\rho$ is the bulk density of the sample. The transmittance is defined as the ratio of $I/I_o$. The absorbance can also change, indirectly, with the temperature of the sample due to thermal expansion, dissociation of the hydrogen bonds, and changes in the populations of energy levels which are associated with the absorption of light intensity. Analogous expressions to the above can be developed for reflectance spectra so that the properties of opaque substances can be similarly correlated with spectral information.

The spectral correlations developed for use in spectrophotometric devices in accordance with the present invention are generally built utilizing most or much of the spectrum of the sample although suitable correlations can also be developed using the absorbances measured at a few select wavelengths. Although a spectrum can consist of several hundred intensities measured at different wavelengths, many of these data points are highly interdependent, or colinear. Multivariate regression can be used to simplify the spectrum into latent variables which describe the independent variations in the spectra for a set of samples. The scores or relative magnitudes of the latent variables in the spectrum change as the properties of the sample change. The number of latent variables necessary to accurately model a system generally depends on the system being analyzed. Generally, the properties can be modeled using less than 20 latent variables, frequently less than 10 latent variables, and often less than 6 latent variables. The number of latent variables minimally necessary to predict stream properties can be estimated using splitting techniques, PRESS statistics, by plots of variance fit using successive numbers of latent variables, or other forms of statistical analysis.

A spectrophotometer in accordance with the principals of the present invention, can span a broad wavelength range of from about 100 nanometers to about 2,500 nanometers where the particular feedstock necessitates absorption determinations at a wide range of wavelengths. Generally, the spectrophotometer is designed to span a range of from about 100 nanometers to about 2,500 nanometers, as narrow as from about 800 nanometers to about 1,100 nanometers, or even as narrow as from about 850 nanometers to about 1,000 nanometers.

Spectrophotometers in accordance with the present invention and spanning the range of from about 850 nanometers to about 1,000 nanometers include the third overtone of the carbon-hydrogen stretching mode (850 nanometers to about 960 nanometers) and the second overtone of the oxygen-hydrogen stretching mode (960 nanometers to about 990 nanometers). The third combination band of the carbon-hydrogen stretching and bending modes is found at 1000 nanometers to about 1120 nanometers. However, the spectra of the third combination band can be noisy when the photoresponse is measured on silicon detectors, found in photodiode arrays attendant to many spectrophotometers. Spectrophotometers measuring the properties of hydrocarbons and oxygenated hydrocarbons that are found in transparent liquid hydrocarbon products can generally analyze the properties of such a sample across a wavelength range of about 800 nanometers to about 1100 nanometers. Similarly, the more useful spectral ranges for analyzing crude petroleums and other black oils are from about 1300 nanometers to about 1500 nanometers and/or from about 1600 nanometers to about 1800 nanometers, depending on the extent to which absorbances due to electronic transitions interfere with these vibrational bands of the hydrocarbon oil and the properly being monitored.

FIG. 1 is a diagram of a spectrophotometer in accordance with the principals of the present invention. The light source 1 can be any suitable polychromatic light source such as mercury vapor, or deuterium lamps, or tungsten filament lamps filled with an inert gas such as, but not limited to, krypton, with the filament under vacuum or with a halogen at low pressure. The preferred polychromatic light source is a tungsten-halogen lamp powered by a constant voltage or constant current supply. The output of light source 1 is launched through single lens 2 into fiber optic cable 3.

Fiber optic cable suitable for use in the spectrophotometer of the present invention has a core diameter ranging from about 50 $\mu$m to about 1000 $\mu$m, preferably from about 100 $\mu$m to about 400 $\mu$m, and more preferably from about 100 $\mu$m to about 250 $\mu$m, for best results. The preferred material for the core of the fiber optic cable is silica with a low hydroxyl content of below about 50 ppm, or any other material that is substantially transparent to light in the wavelength region of interest. The fiber optic cable can be externally cladded for light reflection to maintain the light within the fiber optic cable. Suitable cladding materials for silica fibers can include doped glasses, fluorocarbons, and mixtures thereof. The preferred fiber optic cable cladding materials are fluorocarbons for conducting light through the high-efficiency fiber optic switches 4 and mode scrambler 15, whereas the preferred cladding material for long fiber optic runs, such as from the light source 1 to the upstream high-efficiency fiber optic switch 5 and from the downstream fiber optic switch 6 to the mode scrambler 15, is doped glass. Single fiber optic strands are preferred over other alternatives, including fiber optic bundles, in the apparatus of the present invention. Fiber optic strands generally reduce the cost of the apparatus, are more durable, improve flexibility of application, and provide for more precise photometric measurement.

The routing of light through the optics is controlled by at least one and preferably two high-efficiency light switches 4 consisting of upstream light switch 5 and downstream light switch 6. Alternatively, a single high-efficiency switch 5 and an optical coupler 6, or vice versa can be used. An optical coupler is a device that directs light from two or more fiber optic cables into a single fiber optic cable or vice versa. Common coupling devices include, but are not limited to fusion splices, mechanical splices, and passive taps. While coupling devices can be used, orientations featuring optical couplers are generally less efficient and are not preferred. In the present invention, fiber optic switches and/or couplers are used in place of shutters, choppers, beam splitters, moving mirrors, and other means common to prior art spectrophotometers. The fiber optic components provide the advantages of low cost, reliability, ruggedness, and reduced size, particularly beneficial for process analyzer applications common in a field or manufacturing plant environment.

The polychromatic light from light source 1 can be directed in either of two primary directions: the sample channel direction or the reference channel direction. The spectrum of light intensity is alternatively measured through the sample and reference channels in order to compensate for photometric drift. Polychromatic light generally travels through the sample channel direction when the high-efficiency light switches 4 are aligned to direct the polychromatic light to the sample cell 7 through fiber optic cable 8 and return the polychromatic light to downstream light switch 6 through fiber optic cable 9. Polychromatic light passes through the sample cell 7 where it is passed through sample stream 23 to be analyzed, strikes a prism or retroreflector 10, passes through sample stream 23 again, and is returned to fiber optic cable 9. Alternatively, the light can be directed through the sample in a single pass cell where the light is imaged from fiber optic cable 8, through the sample, and into fiber optic cable 9 using at least one single or multi-element lens. In the preferred embodiment, two lenses are used to couple the light between fiber optic cables 8 and 9, and to collimate the light passing through the sample.

The spectrophotometer of the present invention can have a plurality of sample channels and reference channels. The spectrophotometer can also have a plurality of sample channels with one reference channel. The channels can gain access to the polychromatic light source through a fiber optic manifolding system. In this manner, the same primary spectrophotometric hardware can be utilized to analyze a plurality of sample streams for a plurality of physical properties. This system can be controlled by multiplexing devices that function utilizing switching devices including, but not limited to, mechanical motion mechanisms that align the fiber optics launching and receiving the light.

The high-efficiency fiber optic switches suitable for use in the spectrophotometer of the present invention are generally mechanical motion mechanism types and solid state types where a liquid crystal becomes either transparent or reflective through the application of an electric or electromagnetic field. The preferred high-efficiency fiber optic switches are latching type mechanical motion switches. The latching type switches generally work by moving a fiber optic cable from port to port and rely on the alignment of the launching and receiving fiber optics to maintain efficient transmission of the light. Generally, no optical elements are placed between the launching and receiving fiber optic cables. However, optical elements, and in particular, one or more single or multi-element lenses, could be placed between the lauching and receiving fiber optic cables, but this can compromise the efficient coupling of light between the fiber optic cables. The high-efficiency fiber optic switches can cycle between sample and reference ports at frequencies ranging from about 100 to 0.001 cycles per second, preferably from about 10 to about 0.01 cycles per second, and more preferably from about 1 to about 0.1 cycles per second, for best results. Insufficient sample and reference cycling may not provide adequate reduction of photometric drift while excessive sample and reference cycling can introduce additional noise in the spectrum. The high-efficiency fiber optic switches of the present invention couple more than 50%, generally more than 75%, and often more than 90% of the light from the launching fiber into the receiving fiber.

The sample cell, suitable for use in the spectrophotometer of the present invention can be designed for insertion into the sample source directly or can be accessed by conveying a slip-stream of the sample from the sample source to the sample cell utilizing a conveying device or conduit such as sample tubing. Suitable locations for insertion of the sample cell, can be, but are not limited to pipelines, process vessels, distillation towers, and the like. The preferable location for sample cell insertion is generally at a reasonably constant stream temperature and pressure, with fluid turbulence in the optical path of the sample cell kept to a minimum. These parameters are not essential to obtaining accurate analyses but can improve the quality and consistency of the results.

The sample cell itself, can be designed to direct light through the sample in a manner such that light passes through the sample at least once and preferably twice. Where sampling is done through use of a slip-stream, the sample cell can be a once through single pass type where the fiber optics that launch and receive light are located at opposite ends of the cell and one or more lenses are used to direct light in and out of the two fiber optic cables. Where sampling is done through use of an insertion probe, two or more passes are generally preferred such that the fiber optic cables launching light into, and receiving light from the sample cell can be placed at the same end of the sample cell. The polychromatic light can be reflected at the end of the sample cell opposite the fiber optic cables, in a two pass sample cell, where the reflecting prism reflects the light at least twice and preferably three times in order to insure accurate reimaging on the outlet fiber optic cable. The sample can be isolated from the fiber optic cables by a plurality of windows and preferably two windows sealed on O-rings or gaskets. The total path length of the sample, described previously as L, is generally between about 0.1 mm and 1000 mm, preferably between about 10 mm and 300 mm, and more preferably between about 50 mm and 200 mm, for best results. Shorter path lengths can result in inadequate light absorption by the sample, while excessively long path lengths can result in over-absorption of light and imprecise results.

The polychromatic light from light source 1 can also travel through the reference channel direction when the high-efficiency light switches 4 are aligned to direct the polychromatic light to the attenuator 11 through fiber optic cable 12 and return the polychromatic light to downstream light switch 6 through fiber optic cable 13. The attenuator is utilized to balance the polychromatic light transmission between the reference and sample channels and to ensure reproducible imaging of the light into the fiber optic cable 13.

Attenuation devices suitable for use in the spectrophotometer of the present invention can consist of one or more lenses, fiber optic cable, and can be made without optics by separating the two fiber optics with one or more coupling devices. The preferred attenuation device consists of two plano convex lenses or two achromatic doublet lenses in series, with screens or other devices optionally placed between the lenses to provide achromatic attenuation of light launched between the fiber optic cables.

The polychromatic light passing through downstream high-efficiency light switch 6 is routed through fiber optic cable 14 to a mode scrambler 15. High-efficiency fiber optic switches, upon cycling, may not provide reproducible imaging of the light into the spectrograph. This can result from mode noise whereby the angular distribution of light emerging from the fiber optic into the spectrograph is sensitive to slight misalignment of the launching and receiving fibers in the high-efficiency fiber optic switches. This problem is solved by providing a mode scrambler 15 to reproducibly and uniformly image light from the fiber optic cable into the spectrograph 17.

The mode noise occurs because the fiber optics are optical elements with imaging properties and are not merely conduits for transmitting light through the spectrophotometer. When the mechanical alignment of the fibers in the high-efficiency fiber optic switches, or the alignment of any other optical elements between the light source and spectrograph is changed, the image launched from the fiber into the spectrograph can be altered. This irreproducibility is manifested as noise in the spectral image measured on the photodetector. When light is passed through several hundred feet of fiber optic cable, the image presented to the fiber is altered due to scattering by bends, cracks, and other imperfections in the fiber. Thus, the image presented from a long run of fiber optic cable is scrambled, and the light traveling through the fiber assumes an equilibrium distribution of modes or states in the fiber just as a fluid moving through a pipe develops an equilibrium velocity distribution across the diamter of the pipe. Once the equilibrium mode distribution is obtained, the image emerging from the fiber optic cable is uniform in that the relative light intensity emerging at any angle relative to the axis of the fiber is substantially independent of the way in which light was launched into the fiber and is characteristic of the type of fiber optic cable used to transmit the light.

While several hundred feet of fiber optic cable may be used to affect mode scrambling, short lengths of fiber optic cable may be used if bends, cracks, and other imperfections are systematically introduced across the length of the fiber optic cable. For example, the mode scrambler can comprise from about 1 to about 20 runs of fiber optic cable turned around two spools in a fogure eight pattern, where the spools range in diameter from about 0.125 inches to about 5.0 inches. The mode scrambling objectives can also be achieved by the more costly means of providing a fiber optic cable run between the downstream high-efficiency fiber optic switch 6 and the spectrograph 17 of from about 10 feet to about 10,000 feet, preferably from about 100 feet to about 5,000 feet, and more preferably from about 200 feet to about 2,000 feet, for best results. It is understood that other mode scrambling means can be used to alter the image, or angular distribution of light in the fiber optics, so that a uniform and reproducible image is obtained when the light is launched from the fiber optic into the spectrograph; and the aforementioned mode scrambling means are intended to be illustrative rather than limiting.

In addition to compensating for slight irreproducibilities in the mechanical alignment of the fibers, which occurs upon cycling the high-efficiency fiber optic switches, the mode scrambler also mitigates the effects of selectively altering the transmission of light through either the sample or reference channels. Such effects are normally manifested in the background spectrum, described below, and the magnitude of these effects is substantially reduced by the use of a mode scrambler in the fiber optic network. Effects that can be mitigated by the mode scrambler include those caused by bending the fiber optic cable, breaking and remarking the fiber optic connections, and refocusing the optics in the sample cell or attenuator. Thus, the mode scrambler is generally useful in any spectrophotometer using fiber optics for the transmission of light, where the reproducible imaging of light into or out of the fibers is important to obtaining reproducible spectral measurements.

The polychromatic light from the mode scrambler 15 is passed through fiber optic cable 16 to the spectrograph 17. Although any wavelength discrimination device or means for separating the polychromatic light by wavelength and detecting the light intensity at each wavelength can be used, the preferred means includes a fixed diffraction grating 18 and a photodiode array detector 19. The polychromatic light from fiber optic cable 16 is launched onto the fixed diffraction grating 18 which diffracts and reflects the light onto the photodiode array detector 19. Spectrophotometers having additional optical elements in the spectrograph can also be used.

Photosensitive array detectors suitable for use with the present invention generally measure light intensity at all points in the spectrum simultaneously. Each photosensor, or pixel, in the array generally measures the light intensity over a narrow range of wavelength so that, taken together, the signals from all photosensors in the array constitute the spectrum. Pixels generally correlate to the precise locations where light was diffracted on and reflected from, the fixed diffraction grating. Photosensitive array detectors suitable for use with the apparatus of the present invention generally have at least 100 pixels spanning the corresponding wavelength range of particular interest, preferably at least 200 pixels, and more preferably at least 500 pixels for best results. Corresponding spatial resolutions suitable for use with the apparatus of the present invention should be at least 1 pixel per nanometer, preferably at least 2 pixels per nanometer, and more preferably at least 4 pixels per nanometer for best results. The optical wavelength resolution of the spectrophotometer should be better than 8 nanometers, preferably better than 4 nanometers, and more preferably better than 2 nanometers for best results. Suitable photosensitive array detectors for use in the spectrograph of the present invention can comprise metallurgy such as indium/gallium/arsenide, germanium, silicon, platinum silicide, with silicon being the preferred metallurgy for transparent liquid petroleum products and indium/gallium/arsenide being the preferred metallurgy for crude petroleums.

The photosensitive array in accordance with the apparatus of the present invention generally measures light intensity, which can be converted proportionally to an electrical signal. Suitable means for this conversion can include any one of a number of solid state electronic devices, including, but not limited to photodiode arrays, charge-coupled devices (CCD arrays), and optical sensor arrays, with the photodiode array being the preferred means for converting light into electric signals. The solid state electronic device serves to convert the light signal to an electrical signal which is proportional to the light intensity. Thus the light intensity is converted to a electrical current, voltage, or charge signal which can be used as a convenient measure of light intensity. In this manner, spectra are generally displayed with wavelength or pixel orientation on the x-axis and light intensity as measured by electrical current, voltage, or charge on the y-axis.

Light intensity spectra are the raw spectral images generated in the spectrophotometer. The light intensity spectra are generally used when spectral information and particularly chemometric models are to be passed among spectrophotometers, because the mathematics for doing so are relatively straightforward. Transmittance and absorbance spectra are non-linear combinations of the intensity spectra of the sample and the reference channels. These combinations, and in particular, absorbance, are most useful for generating chemometric models because absorbance is proportional to the concentration of the light absorbing material and these combinations are less sensitive to drift and other aberrations caused by imperfections in the spectrophotometer.

A spectrograph in accordance with the spectrophotometer of the present invention, can utilize a temperature expansion resistant materials for mounting the optical elements, as compared to aluminum mounting plates, which have previously been used in the art. The coefficient of thermal expansion of aluminum is about $23 \times 10^{-6}/°C$. and can produce a spectral shift of as much as 1 nanometer or more for a 3″ spectrograph chassis over a 60° C. temperature change. Use of temperature expansion resistant materials can substantially minimize spectral shifts and increase resultant prediction precision. The temperature expansion resistant material suitable for use in the present apparatus generally has a coefficient of thermal expansion of less than $10 \times 10^{-6}/°C.$, preferably less than $5 \times 10^{-6}/°C.$, and more preferably less than $2 \times 10^{-6}/°C.$, for best results. Suitable materials for use as the temperature expansion resistant mounting plate can include, but are not limited to carbon and graphite fibers in a suitable binder or matrix system. Examples of fiber matrix or binders suitable for use in the present invention can include epoxy, thermosets, and thermoplastics. The preferred temperature expansion resistant materials are the carbon fibers and graphite fibers having epoxy binders. A suitable material for use in the present invention is Quasi-Isotropic Layup with P-75 Pitch-based Graphite Fiber manufactured by Amoco Performance Products.

Driver and Interface boards 20 are provided to drive the photodiode array detector 19, sequence the pixel readings, and amplify the signals prior to the analog to digital converter (ADC) 21. The interface boards 20 can comprise an amplifier section for conditioning the analog signal to the ADC 21, a crystal clock section for precisely sequencing the reading of the pixels, and/or a digital section for synchronizing the reading of the photoarray detector and triggering the ADC 21. The scan rate for scanning the photodiode array director 19 can be adjusted through the driver and interface boards 20 and generally ranges from about 10 to about 10 million pixels per second, preferably from about 1,000 to about 100,000 pixels per second, and more preferably from about 10,000 to about 100,000 pixels per second for best results.

The ADC 21 converts the light intensities from the photodiode array detector 19 into digital signals and is designed to be compatible with computer 22 or other means to digitally process spectral information. The computer 22 is provided to acquire, store, display, and analyze the spectra.

A computer suitable for use in the spectrophotometer of the present invention generally has a means for interfacing with the ADC, optional means for reading other analog signals, such as sample temperature, digital I/O ports for controlling and sensing the status of the photodiode array and fiber optic switches, a central processing unit (CPU), random access memory (RAM), hard or floppy discs or other means for mass storage, a keyboard or other means for entering property data for calibration, an optional display means for reporting and trending determinations from the analyzer, and a serial port or other means for transmitting determinations from the analyzer to a human or process control interface.

Spectrophotometers similar to that described in FIG. 1 and in accordance with the spectrophotometer of the present invention generally function by launching polychromatic light having a wavelength ranging between from about 100 nanometers to about 2500 nanometers, preferably from about 800 nanometers to about 2500 nanometers, and more preferably from about 800 nanometers to about 1100 nanometers, alternatively through at least one sample channel and at least one reference channel, utilizing at least one high-efficiency fiber optic switch 4. The reference and sample channel cycling is performed in order to self-reference the apparatus and substantially correct for photometric drift.

The sample to be analyzed is directed to a sample cell 7 along with polychromatic light from along the sample channel, whereby the polychromatic light is passed through the sample. The polychromatic light can be passed through the sample once or preferably at least twice utilizing a prism or light reflection device. In multiply passing the polychromatic light through the sample, the light can be reflected two or more times. Some of the light is absorbed by the sample and some of the light passes or is transmitted through the sample and becomes sample spectral information.

The polychromatic light along the reference channel is attenuated in order to balance the polychromatic light transmission between the reference and sample channels. The light that is transmitted through the attenuator 11 is termed attenuated reference spectral information.

The sample spectral information from the sample channel and the attenuated reference spectral information are routed alternately to a mode scrambler 15 for reproducibly imaging light into the spectrograph 17 in a subsequent step. The sample spectral information and the attenuated reference spectral information from the mode scrambler 15 is then processed in a spectrograph 17 wherein the sample spectral information and the attenuated reference spectral information are separated by wavelength using a wavelength discrimination means and the light intensity for each wavelength is measured using a photosensitive detector. In the preferred embodiment, a fixed diffraction grating 18 and photodiode array detector 19 are used for wavelength discrimination and detection. The absorbance spectrum is then calculated from the diffracted and recorded sample spectral information and attenuated reference spectral information, and an appropriate chemometric model applied to the absorbance spectrum to predict the physical properties of the sample.

The reference channel measurement steps are provided to permit correction of the device for physical or mechanical changes that occur upstream of the upstream high-efficiency light switch 5 or downstream of the downstream high-efficiency light switch 6. Physical changes in the device itself, the testing conditions, or any of a number of other events can create imprecision in the spectrophotometric readings. The spectrophotometric readings are also subject to photometric drift over time. Photometric drift can originate in the light source, the fiber optic cables, or other optical components, as well as the electronics utilized for measuring light intensity. Since polychromatic light travels through the same path through both the sample and reference channels, but for the fiber optic cable and other devices between the high-efficiency fiber optic switches, physical and mechanical changes and photometric drift that occur upstream or downstream of the high-efficiency fiber optic switches 4 can be factored out.

The light intensity signal measured on the sample channel is generally quantified by the following expression:

$$S_s = S_d + a_c a_s g I_o (e^{-A})$$

where $e$ is the base of the natural logarithm, $S_d$ is the dark signal; $a_c$ is the attenuation, or reduction in the amplitude of the light signal in the optics common to the signal and reference channels; $a_s$ is the attenuation in the optics unique to the sample channel; and g is the photometric gain (i.e. light intensity to electrical signal conversion factor). The dark signal, $S_d$, can be determined by measuring light intensity with the high-efficiency fiber optic switches juxtaposed with one of the switches directed towards the sample channel and the other switch directed towards the reference channel. The dark signal is measured and defined as the zero point of the light intensity or y-axis.

The light intensity signal measured on the reference channel is generally quantified by the following expression;

$$S_r = S_d + a_c a_r g I_o$$

where $a_r$ is the attenuation in the optics unique to the reference channel.

The apparent absorbance measured on a dual channel spectrophotometer is defined by the following expression:

$$A_a = \log[(S_r - S_d)/(S_s - S_d)] = A_b + \epsilon L \rho W$$

where the background spectrum is defined as $A_b = \log(a_r/a_s)$ and reflects the difference in light absorbance between the reference and sample paths with no sample present. The apparent absorbance, $A_a$, the background spectrum, $A_b$, the absorption coefficient, $\epsilon$, and to some extent, the path length L, are wavelength dependent. The apparent absorbance, $A_a$, in the dual channel instrument of the present invention is substantially independent of the light intensity incident on the sample, $I_o$, common mode attenuation, $a_c$, and the photometric gain, g. In this manner, the apparatus of the present invention eliminates potential error sources by rendering them substantially irrelevant.

Filtering steps can be provided for removing high frequency noise and baseline drift from the absorbance spectrum. The absorbance spectrum, in its unfiltered form, can be subject to high frequency noise, or the scattering of points above and below the absorbance spectrum generally caused by the electronics or optics. The absorbance spectrum, in its unfiltered form, can also experience baseline drift. Baseline drift occurs where the absorption baseline or slope of the baseline begins to drift upwards or downwards. Baseline drift generally is a form of low frequency noise and can be caused by drift in the electronics, scattering by the sample, fouling of optical surfaces, or thermal expansion in the optics. High frequency noise and baseline drift can be eliminated by a filtering step.

Filtering high frequency noise can be performed by smoothing or weight-averaging adjacent data points. Common algorithms for smoothing spectra can include Fourier filters, best-fit polynomials, Gaussian or binomial filters, and binning or adding groups of adjacent data points. Binomial filters are used most commonly since most of the methods provide similar accuracy while the binomial filters are easier to implement. Suitable binomial filters can include utilizing from 1 to about 20 smoothing iterations with a 1:2:1 weighting function, with 4 to 8 smoothing iterations being preferred. The extent of high frequency filtering is generally controlled by varying the number of points in the smoothing algorithm. Binning methods can also be attractive since fewer data points can be used to represent the spectrum, thereby increasing computational speed.

Filtering low frequency noise or baseline drift is most commonly performed by differentiation. The extent of low frequency filtering is generally controlled by taking successive derivatives with one derivative being preferred for the present invention.

Chemometric models which relate the spectral data to the desired physical properties of the sample can be generated by any of the several currently available methods or combinations thereof. The simplest is multiple linear regression (MLR), where the absorbance, or a suitable measure of light intensity, at various wavelengths can be correlated with the physical property to be determined. Once the correlation has been established, physical properties of subsequent samples can be measured based on correlation coefficients and the spectrum of the sample. MLR utilizes only a small portion of the information available in the spectrum and such models can be more sensitive to errors caused by colinearity or intercorrelations of the absorbance determinations made at the various wavelengths of interest.

The methods of factor analysis and latent variable determination have been developed to use more of the information available in the spectrum and to manage the effects of colinearity. In principle component regression (PCR), successive factors or latent variables are calculated where successive latent variables are correlated to the spectra of the samples in order of contribution to the total absorbance until substantially all of the absorbance can be described using linear combinations of the latent variables. Each of the latent variables calculated in PCR is independent or orthogonal to the other latent variables and therefore accommodates colinearity in the spectral information. Once the latent variables are determined, they are then correlated with the physical property of interest. In PCR, the spectral information is reduced to latent variables without consideration as to how the latent variables relate to the property of interest.

In partial least squares (PLS), the latent variables are determined in order of contribution to the total absorbance and one or more of the physical properties that are the dependent variables. Thus, the latent variables of a PLS regression are maximally correlated to both the spectral and physical property data. Once a chemometric model is built using MLR, PCR, PLS, or similar means, the model can be applied to the spectrum of an unknown to predict one or more of its physical properties. For example, a suitable software package that implements these methods and builds chemometric models is SpectraCalc by Galactic. The derived chemometric model is then tested using samples of unknowns that were not used for developing the model.

The apparatus of the present invention functions best when key parameters that can affect the prediction precision and accuracy of the spectrophotometer are identified and controlled. These parameters to be controlled can include wavelength precision, photometric precision, photometric linearity, sampling time, changes in or adjustments to the optical path, high-efficiency fiber optic switch repeatability, sample temperature, sample flowrate, and environmental effects.

Shifts in the wavelength axis or wavelength drift can occur as a result of mechanical vibration or shock and changes in the temperature of the spectrograph. Wavelength drift compromises prediction accuracy by changing the wavelength range corresponding to each detector element of the photo-sensitive array. The accuracy of chemometric predictions can be noticeably effected where the spectrum is shifted by 0.03 nanometers or more. Where the spectrum is shifted by more than 0.3 nanometers, the resulting predictions may not be sufficiently accurate for use in some process services.

Methods to reduce or compensate for the effects of wavelength drift generally include improving spectrograph design, controlling or compensating for changes in the temperature of the spectrograph, and isolating the spectrograph from or mitigating the effects of mechanical vibrations or shock. A light source that emits over a narrow wavelength range, such as a laser diode can be integrated into the optics in order to provide a reference point for compensating for wavelength drift. Methods may also be utilized to maintain a substantially constant spectrograph temperature. These methods can include an ambient temperature controlled environment for the spectrograph and/or a temperature control system that monitors the spectrograph temperature and either controls or compensates for temperature changes mathematically within the chemometric model. Where a system is designed to maintain a substantially constant spectrograph temperature, the spectrograph temperature should be maintained within a total range of about 20° F., preferably within a range of about 10° F., and more preferably within a range of about 5° F. for best results.

Changes in photometric output can occur as a result of movement or changes in the optics, particularly those in the sample and reference paths between the high-efficiency fiber optic switches, changes in the level of stray light in the spectrograph (often caused by scattering from the diffraction grating), noise, and non-linearity in the photo-electronics. Changes in photometric output can compromise chemometric prediction precision by selectively emphasizing or deemphasizing portions of the spectrum, which can alter predictions from the chemometric models. The degree of photometric precision required to provide chemometric prediction precision can vary depending on the particular drift or inaccuracy introduced. For example, stray light levels above 0.1% of full scale intensity, wherein full scale intensity is defined as the amount of light needed to saturate the photodiode array detector during the period between readings of the detector, can effect the precision of chemometric predictions, while noise levels above 0.03% of full scale intensity can effect chemometric prediction precision. Therefore, the degree of photometric precision required for precise chemometric prediction generally depends on the particular source of the photometric drift. Generally, photometric precision levels of less than 0.03% of full scale intensity can ensure precise and reliable chemometric prediction performance in the apparatus of the present invention.

Methods to ensure photometric precision generally constrain the design of the spectrophotometer. These methods include the design of the photoelectronics to maintain photometric linearity, utilizing fiber optic cable runs for the sample and reference channels that are as short as possible and held as rigid as possible (note that there are no similar restrictions on the fiber optic path common to the sample and reference channels), designing the diffraction grating to minimize the generation of stray light, designing the spectrograph to minimize the reflecting of stray light onto the photodetector, and using a mode scrambler to ensure the uniform and reproducible imaging of light into the spectrophotometer.

Photometric linearity is a particularly important component of photometric accuracy. The degree of photometric linearity is an indication of how accurately the light intensity signal is transformed into a proportional electrical signal. Photometric linearity is generally a function of the inherent linearity of the photodector and the ability of the photoelectronics to produce an electrical signal that is proportional to light intensity. Shifts in photometric linearity can compromise prediction accuracy by distorting the absorbance determinations. For best results, the photometric response of the apparatus of the present invention should be linear to better than 0.9% of full scale intensity and preferably better than 0.2% of full scale intensity.

Methods to maintain or improve photometric linearity include designing the photoelectronics to provide a signal that is proportional to the light intensity incident on the detector and operating the photodiode array detector outside of saturation. The response of photodiode array detectors, when operating near saturation, can become non-linear. Non-linearity due to photodiode array detector saturation can be substantially reduced or eliminated by operating the photodiode array detector at less than 85% of full scale intensity.

The sampling time is the amount of time that polychromatic light is being launched through the sample and is generally quantified in terms of number of scans. Sampling time, in contradistinction to some of the other variables, is a controllable parameter, and can be adjusted for optimum precision. While sampling time is easily controllable, it has only minimal effect on the precision of chemometric predictions when the noise level in the photoelectronics is small. For example, predictions from a single scan can be as precise as those obtained from 1000 scans providing the signal to noise ratio in the intensity spectra for the sample and reference channels exceeds 3000:1 over the spectral range of interest.

While sampling time can have minimal effect on prediction precision, sampling rate can have a substantial effect on chemometric prediction precision. Where high sampling rates cause the electronics to reach peak speeds, the photo-detection circuitry can cause photometric non-linearity as described above. A suitable method for controlling sampling rate is to reduce the light source intensity and select a slower sampling rate that maintains photodiode array detector load from about 75% to about 85% of saturation in portions of the spectrum where the light intensity is greatest, in order to assure substantial photometric linearity.

Changes in or adjustments to the optical path between the high-efficiency fiber optic switches should generally be monitored with particular diligence. Changes made outside of the sample and reference paths (i.e., outside of the high-efficiency fiber optic switches), generally result in minimal effects to prediction precision. This is due to the fact that these changes are common to both the sample and reference channels and are essentially offsetting in the absorbance determination. Changes made within the sample or reference path can result in prediction errors. These changes can include replacement of the high-efficiency fiber optic switches, replacement of a sample cell, or changes or movement in the fiber optic cables between the high-efficiency fiber optic switches. The mode scrambler and attenuator of the present invention generally reduces the adverse effects of changes or adjustments made between the high-efficiency fiber optic switches. Where changes or adjustments are made between the high-efficiency fiber optic switches, these changes can be further offset by adjusting for changes in the background spectrum. The background spectrum can be determined by sampling an optically inert material such as dry air, carbon tetrachloride, carbon disulfide, or fluorinert, and measuring the corresponding absorbance spectrum. The tolerance of the apparatus of the present invention to changes or adjustments to the optical path render the device particularly suited to the rugged environment encountered in many manufacturing facilities.

The repeatability of the high-efficiency fiber optic switches can affect the precision of chemometric predictions by creating noise and causing or contributing to drift in the background spectrum. Noise can be similarly produced by bending the fiber optic cables, by misaligning the fibers in the high-efficiency fiber optic switches, and accentuated or diminished through use of different materials for the fiber optic cables and switches. Generally, fiber optic switches and cable made from fluorocarbon clad fibers perform better than glass clad fiber although both are suitable for use in the present invention. Noise created from all of the above described sources is substantially reduced through use of the mode scrambler. Noise or irreproducibilities in the measured absorbance spectra created from cycling the high-efficiency fiber optic switches, can be reduced by a factor of 2, a factor of 3, and even as much as a factor of 5 by addition of the mode scrambler of the present invention.

The sample temperature can affect prediction precision by changing the density of a sample and its resultant absorbance as described in a previous equation. The density or inversely, the volume expansion for hydrocarbons common in petroleum refineries can often range from about 0.02%/°F. to about 0.4%/°F. depending on the particular hydrocarbon and the particular temperature range. Suitable methods for mitigating the effects of sample temperature on prediction precision include sample conditioning or maintaining the sample temperature substantially constant, monitoring the sample temperature and correcting for the effects mathematically, among other methods known in the art. Monitoring the sample temperature and mathematically correcting for temperature deviations from a target is simple and requires a thermocouple and software steps. However, temperature expansion effects are generally not linear and correction models, under some situations, may have to account for this non-linearity. Maintaining a constant sample temperature by sample conditioning can eliminate inaccuracies inherent to a temperature to volume expansion correlation, but generally requires a potentially awkward heat exchange step to ensure proper temperature control. The sample temperature in a constant sample temperature device generally should be kept within a range of about 40° F. and more preferably within a range of about 20° F. for best results when monitoring the properties of hydrocarbons. Sample temperature conditioning is particularly important when effects other than thermal expansion, which introduce structure or other non-systematic changes in the spectra, cause the spectrum to less predictably change with temperature. In instances where hydrogen bonding is prevalent, such as in mixtures containing alcohols, sample temperature ranges may need to be controlled to within 1° F., for best results.

The sample flowrate can effect prediction precision by the presence of variations in the amount of gas bubbles or in the magnitude of density fluctuations in the sample stream. These variations, which can result in undesirable and uncompensated attenuation, can be caused or effected by the level of turbulence at different flowrates. Where the sample is provided by a slipstream, flowrates can be adjusted to affect proper operation. Where the sample cell is an insertion-type probe, the sample flow may be reduced by modifying the sample cell itself or lowering the supply line pressure. Generally, sample flowrate does not substantially effect chemometric prediction precision as long as a suitable amount of sample passes through the sample cell. Suitable sample velocities in the sample cell are generally less than about 10 ft/sec and more preferably less than about 1 ft/sec for best results.

Environmental effects such as the introduction of non-sample related absorbing components to the spectrum, can also effect prediction precision. Non-sample related components such as hydrocarbon or water in the form of smoke, hydrocarbon vapors, water vapor or humidity, can appear in the sample and/or reference spectra, introduced through points in spectrophotometric equipment where optical components are not entirely enclosed. Optical components having optical cavities where the polychromatic light is exposed to the environment can include the lamp source, the attenuator, the high-efficiency fiber optic switches or optical coupler, the sample cell, and the spectrograph. Non-sample related components which enter the system upstream of the first fiber optic switch or downstream of the second fiber optic switch or optical coupler are generally less damaging to prediction precision since these areas are common to both the reference and sample channels.

Non-sample related absorbing components can be minimized by purging of the particular cavities with a non-absorbing gas. Suitable non-absorbing gases can include, but are not limited to dry and hydrocarbon-free nitrogen, air, argon, helium, krypton, and radon. The preferred non-absorbing purge gases are dry nitrogen and air. Purging of the optical cavities can be performed on a continuous basis or can be performed selectively. Where purging is performed continuously, the purge rate should range from about 0.01 CFM to about 10 CFM to insure sufficient optical cavity displacement. In a selective purge system, it is recommended that purging be performed each time an optical cavity is exposed to the environment. Upon exposure, the optical cavity space should be replaced by 5 and preferably 10 times the vapor space of the non-absorbing gas at atmospheric conditions. After purging with a suitable amount of non-absorbing purge gas, a positive pressure should be maintained on the sealed cavity in lieu of maintaining a constant purge rate. This method may be preferred where safety or non-absorbing gas usage are of particular concern and it is desirable to minimize the volume of non-absorbing gas emitted to the space surrounding the spectrophotometer.

The present invention provides an apparatus for obtaining spectral information and quantifying the physical properties of a sample that achieves superior chemometric prediction accuracy and is particularly reliable, durable, and stable over time. An apparatus in accordance with the principals of the present invention can generally achieve a prediction accuracy for measuring physical properties of better than plus or minus 1.0%, better than plus or minus 0.5%, and even better than plus or minus 0.2%. A substantial proportion of this prediction error can be, and is generally incurred from the primary analytical method used to quantify the property in building the chemometric model. Corrected for errors inherent in the primary method used in building the chemometric model, the prediction accuracy can be better than plus or minus 0.1% and even better than 0.05%.

The apparatus of the present invention utilizes substantially no moving optical components other than the high-efficiency optical switches and is designed to factor out, substantially reduce, or mitigate imprecision in chemometric predictions generally incurred by prior art devices. When repairs are necessary, such as the routine replacement of the light source or repairs requiring movement of the apparatus or fiber optics, the device is designed to accommodate many of these repairs without requiring costly recalibration of the instrument or redevelopment of the chemometric model.

The present invention provides an apparatus for obtaining spectral information and quantifying the physical properties of a sample that does not utilize fiber optic bundles or incur the inherent costs and imprecisions of fiber optic bundles. By eliminating use of fiber optic bundles, discernable artifacts in the absorbance spectra which are caused by small differences in the launching of light into and out of each fiber strand in the fiber optic bundle, and changes in these small differences with time, are eliminated. Elimination of fiber optic bundles further reduces the need to recalibrate the analyzer and redevelop the chemometric model upon routine maintenance of the analyzer. Moreover, fiber optic bundles can cost from 10 to 100 times more than a single fiber optic strand and render some uses for spectrophotometric analysis cost prohibitive.

The present invention provides an apparatus for obtaining spectral information and quantifying the physical properties of a sample that efficiently and precisely measures the light transmitted through the sample and reference channels of the analyzer with desensitized high-efficiency fiber optic switches and without other diverting devices that rely on the precise mechanical alignment of a critical optical component. The apparatus of the present invention utilizes high-efficiency fiber optic switches resulting in higher signal to noise ratio and improved photometric precision. The high-efficiency fiber optic switches also generally reduce the time required to measure the spectrum. The benefits of the high-efficiency fiber optic switches are accommodated by a mode scrambler, which compensates for variability in the imaging of light from the launching to receiving ports of the fiber optic switches. Addition of the mode scrambler reduces the magnitude of irreproducibilities featured in the spectrum, which are created from the fiber optic switches by a factor of 2, as much as a factor of 3, and even as much as a factor of 5.

The present invention provides an apparatus for obtaining spectral information and quantifying the physical properties of a sample that accurately, reproducibly, and expeditiously resolves wavelength at all relevant wavelengths and is not limited to sequential wavelength measurement. The apparatus of the present invention can measure the spectrum of a sample at any or all of the relevant wavelengths of interest simultaneously, which results in a substantial increase in the speed of spectral analysis. Faster spectral analysis results in faster sampling cycle rates, the analysis of a plurality of samples using the same analyzer device, and/or the reduction or elimination of spectral artifacts caused by a rapid change in the physical or chemical composition of the sample.

The present invention is described in further detail in connection with the following examples, it being understood that the same are for purposes of illustration and not limitation.

EXAMPLE 1

The integrity of the apparatus of the present invention was tested by studying the effects of apparatus and condition variables on measurement accuracy. The variables measured included the effects of filtering the spectra, changing optical components, wavelength precision, photometric precision, photometric linearity, sampling time, changes in the optical path, high-efficiency fiber optic switch repeatability, sample temperature, and sample flow rate.

The sample set utilized in the testing procedure consisted of 29 samples containing varying amounts of n-heptane, iso-octane, toluene, paraxylene, and n-decane. The range of concentrations of the components are described in Table 1.

TABLE 1
STATISTICS FOR THE SAMPLE SET

| Constituent | Concentrations (Wt %) | | |
|---|---|---|---|
| | Minimum | Maximum | Average |
| n-Heptane | 9.86 | 29.84 | 17.50 |
| i-Octane | 9.92 | 29.90 | 20.92 |
| Toluene | 29.96 | 49.95 | 38.75 |
| p-Xylene | 3.94 | 15.28 | 9.41 |
| n-Decane | 1.00 | 32.94 | 13.42 |
| n-Alkanes* | 14.85 | 47.10 | 30.91 |

*wt % n-Alkanes = wt % n-Heptane + wt % n-Decane

Prior to chemometric modeling and physical property prediction, the absorbance spectra were filtered. Unless stated otherwise in succeeding examples, regions outside of the third carbon-hydrogen stretching overtone region (850–965 nanometers) were ignored. The absorbance spectra were differentiated once and then smoothed by convoluting the resulting spectra with a 1:2:1 distribution four times, unless otherwise noted.

Four photometric measurement parameters were utilized to described the tests performed. Transmittance (T) is the ratio of the light intensities transmitted by, and incident on the sample. Absorbance (ABS) is the negative common logarithm of transmittance. Differential absorbance (dABS) is the first derivative of absorbance, computed using the formula:

$$dABS = (T_{n-1} - T_{n+1})/T_n$$

where $T_n$ is the transmittance for the nth pixel. Transmittance, absorbance, and differential absorbance are specific to a particular wavelength. The gross or average efficiency of an optical component is measured in decibels (dB), which is ten times the common logarithm of the ratio of the transmitted to incident power. The average efficiency is generally similar to absorbance except that the average efficiency pertains to a broad spectral range and is scaled differently than absorbance (i.e. $E = -10 A$).

Chemometric models were built for use in these examples using the CPAC PLS program written by the Center for Process Analytical Chemistry at the University of Washington (CPAC). To enhance accuracy, the spectra were scaled by mean centering prior to modeling. Four latent variables were used to model the concentrations of the five components in the sample set.

The effectiveness of the apparatus of the present invention and the quality of the chemometric models were gauged by four statistics. The fitted variance, calculated for the entire spectra and for each component of the sample set, is the fraction of the total variance in the sample set described by the chemometric model. The fitted spectral variance is a measure of how much of the information in the spectra of the sample set is used to model the properties of the sample set, and is determined as the percentage of the variance in the spectra that can be described by the latent variables used to model the component concentrations.

The Standard Error of Estimation (SEE) is an indication of how well the chemometric model fits the sample set. The SEE for each component is a measure of the inherent accuracy of the chemometric model and is determined as the standard deviation between the concentrations predicted using the chemometric model and the laboratory measured values for the 29 samples in the sample set.

The Standard Error of Prediction (SEP) is an indication of how accurately the chemometric model predicts the properties of a test set of samples where the spectra and independent measurements of sample composition were not used in developing the chemometric model. The SEP is determined as the standard deviation between the concentrations predicted using the chemometric model and independent laboratory measurements of sample composition.

The bias is the average offset or mean difference between the values predicted from the spectrophotometer using the chemometric model and the independent laboratory measurements of composition for all samples in the test set.

The effects of the filtering algorithm on the accuracy of chemometric prediction was determined by comparing the accuracy of prediction for models built using the first derivative spectrum in the third overtone band with binomial smoothing over 4 points, the first derivative spectrum in the third overtone band with binning over 4 points, the normalized absorbance spectrum in the third overtone band with binomial smoothing over 4 points spectrum in the third overtone band with binomial smoothing over 4 points where the absorbance across each of the measured spectra was uniformly shifted to give a normalized absorbance of zero (0) near 820 nanometers, the second derivative spectrum in the third overtone band with binomial smoothing over 4 points, the first derivative spectrum in the third overtone band with binomial smoothing over 8 points, the first derivative spectrum in the third overtone band with binning over 8 points, the first derivative spectrum in the third combination band from about 965 nanometers to about 1070 nanometers with binomial smoothing over 8 points, and the first derivative spectrum in the third overtone band and the combination band with binomial smoothing over 8 points. The 4 point smooth was performed using 4 iterations with the 1:2:1 weighting function and the 8 point smooth was performed using 8 iterations with the 1:2:1 weighting function. All overtone and combination bands pertain to vibrational modes which involve the stretching and bending of carbon-hydrogen bonds.

To build the chemometric models, 1000 scans of the spectra were obtained and averaged. The SEE's for each component and model are shown in Table 2, as are the SEPs obtained by averaging 1000 scans of the spectra of unknowns and by using a single style scan to make the predictions of the component concentrations.

body and held in place with rulon bearings. The fiber optic was cemented into a modified SMA connector, having the coupling nut removed and the end machined to 3/16 in and the modified connector and fiber optic was inserted in the same steel body to provide a means for launching light from the source into the fiber optic

TABLE 2

EFFECT OF FILTERING ON THE ACCURACY OF CHEMOMETRIC PREDICTIONS (ERRORS ARE IN WT %)

|  | SEE | SEP 1000 Scans | SEP 1 Scan | SEE | SEP 1000 Scans | SEP 1 Scan | SEE | SEP 1000 Scans | SEP 1 Scan | SEE | SEP 1000 Scans | SEP 1 Scan |
|---|---|---|---|---|---|---|---|---|---|---|---|---|
|  | Overtone Band 1st Derivative Spectrum 4 pt. Smooth | | | Overtone Band 1st Derivative Spectrum 4 pt. Bin | | | Overtone Band Normalized Absorbance | | | Overtone Band 2nd Derivative Spectrum 4 pt. Smooth | | |
| n-Heptane | 0.41 | 0.67 | 0.61 | 0.41 | 0.64 | 0.67 | 0.47 | 3.46 | 3.55 | 0.60 | 1.70 | 5.71 |
| i-Octane | 0.16 | 0.21 | 0.31 | 0.16 | 0.21 | 0.36 | 0.16 | 0.43 | 0.43 | 0.16 | 0.36 | 0.80 |
| Toluene | 0.15 | 0.12 | 0.15 | 0.15 | 0.11 | 0.20 | 0.15 | 0.51 | 0.50 | 0.17 | 0.29 | 0.85 |
| p-Xylene | 0.11 | 0.13 | 0.15 | 0.11 | 0.12 | 0.20 | 0.18 | 1.78 | 1.74 | 0.14 | 0.56 | 1.90 |
| n-Decane | 0.39 | 0.62 | 0.46 | 0.39 | 0.58 | 0.56 | 0.43 | 1.83 | 1.95 | 0.60 | 2.06 | 6.49 |
| n-Alkanes | 0.17 | 0.18 | 0.21 | 0.17 | 0.17 | 0.19 | 0.18 | 1.68 | 1.63 | 0.20 | 0.40 | 0.86 |
|  | Overtone Band 1st Derivative Spectrum 8 pt. Smooth | | | Overtone Band 1st Derivative Spectrum 8 pt. Bin | | | Combination Band 1st Derivative Spectrum 8 pt. Smooth | | | Overtone and Combination Band 1st Derivative Spectrum 8 pt. Smooth | | |
| n-Heptane | 0.41 | 0.68 | 0.61 | 0.41 | 0.59 | 1.00 | 0.43 | 2.80 | 8.79 | 0.40 | 0.75 | 0.87 |
| i-Octane | 0.17 | 0.21 | 0.31 | 0.16 | 0.21 | 0.37 | 0.21 | 0.52 | 3.42 | 0.16 | 0.21 | 0.41 |
| Toluene | 0.15 | 0.11 | 0.15 | 0.15 | 0.12 | 0.23 | 0.43 | 1.73 | 3.24 | 0.15 | 0.10 | 0.14 |
| p-Xylene | 0.11 | 0.12 | 0.15 | 0.11 | 0.13 | 0.22 | 0.48 | 1.84 | 4.13 | 0.11 | 0.12 | 0.20 |
| n-Decane | 0.39 | 0.63 | 0.46 | 0.39 | 0.55 | 0.84 | 0.43 | 2.66 | 7.28 | 0.38 | 0.69 | 0.71 |
| n-Alkanes | 0.17 | 0.18 | 0.21 | 0.17 | 0.16 | 0.21 | 0.17 | 0.24 | 1.65 | 0.17 | 0.18 | 0.22 |

The chemometric models developed from first-derivative spectra were generally more accurate than models built from second-derivative and normalized absorbance spectra. Using the combination band alone or together with the overtone band similarly reduced the accuracy of the models because of noise in the spectra used to build the model. Binomial smoothing and binning provided similar accuracy as did increasing the smoothing iterations from 4 points to 8 points.

EXAMPLE 2

The effects of changing optical components, consistent with utilization of the apparatus of the present invention in a field or manufacturing environment, were measured and compared to the precision of spectrophotometers having components more typical of those used in a laboratory environment. The base spectrophotometer utilized a commercial light source (model 780, manufactured by Newport), a cuvette holder which held cuvettes having a 10 cm path length, no fiber optic switches, no long run of fiber optics or mode scrambler, and no attentuation means. The reference spectra was measured by emptying the cuvette holder.

The first optical component change was use of a different light source. The light source generally have three major components: a lamp, a power supply, and optics for focusing the light into the fiber optics. The new light source was a tungsten-halogen type(Welch-Allyn No. 998319-15) with a lens end of 7 mm D×14 mm F. The filament size was 0.5 mm×1.2 mm. The lamp was designed to run at 5.0 V, 1.8 A, and 2900° K. color temperature. The nominal life was 6000 hours. The power supply (Adtech APS 5-3) had an output of 5.0 V at 3 A. The voltage regulation was 0.1% for a 10% change in line or load. The light from the lamp was focused into the fiber optic cable with a biconvex lens of 10 mm D×10 mm F. An RG780 filter, manufactured by Corning, prevented visible light from entering the spectrophotometer. The glass optics were mounted in a steel cable. In Table 3, the performance of the apparatus having the modified light source is compared to the spectrophotometers having components more typical of those used in a laboratory environment.

The second component change was the addition of two high-efficiency fiber optic switches for use in self-referencing the spectrophotometer to reduce the effects of drift. The high-efficiency fiber optic switches were latching type in a 1×2 configuration (Dicon S-12-L-200). The actual switching was performed by moving the common fiber between the two ports. The coupling efficiency, measured as the light loss across the fiber junction, was 1 db and the minimum switching time was 10 msec or 100 cycles per second. The switches drew 150 mA at 5.0 V. The performance of the apparatus having high-efficiency fiber optic switches is also noted in Table 3.

The third component change was the combination of the high-efficiency fiber optic switches described in the second component change and a long run of fiber optic cable between the downstream high-efficiency fiber optic switch and the spectrograph, for serving as mode scrambling means. The fiber optic cable had a core diameter of 200 μm, a 230 μm fluorocarbon cladding, and a 0.3 NA (Ensign-Bickford HCP-M0200T-06). The core was low-OH silica and the attenuation was of less than 10 db per kilometer of fiber optic cable across the spectral range of from 800 nanometers to 1100 nanometers. The length of fiber optic cable used in the long run was about 700 feet. The performance of the apparatus utilizing high-efficiency fiber optic switches and mode scrambling means is also noted in Table 3.

The fourth component change was the combination of the new light source described in the first component change, the high-efficiency optic switches and mode scrambling means described in the third component change, and the addition of a sample cell. Light was routed into and out of the sample cell with two fiber optic cables, mounted side by side. Light from the first fiber optic cable was collimated with an achromatic doublet lens, passed through the sample, struck a reflection device, passed through the sample again, and was reimaged into the second fiber optic cable with a second achromatic doublet lens. Note that a collimating lens changes the conical distribution of light rays emitted from the fiber optic cable into a set of collimated or parallel rays. The achromatic doublets were 6.25 mm D×12.5 mm F and were mounted to the steel body of the sample cell with Teflon bearings. The reflection device was a retroreflector or corner cube that was slip-fit into the steel body, had a 15 mm D, and was designed to reflect light three times prior to passing the light through the sample the second time. Two windows, 25 mm D×6 mm T, isolated the sample from the optics. The windows were sealed on O-rings. The total path length through the sample (L), was about 10 cm, which provided a maximum absorbance of roughly 0.5 ABS in the 800 nanometer to 1100 nanometer range for typical hydrocarbon materials. The optical attenuation in the cell, including connector losses, was 7 db. Based on a 4% loss at each glass/air interface, the sample cell attenuation was expected to be about 3 db. The performance of the apparatus utilizing the modified light source, high-efficiency fiber optic switches, extended fiber optics, and sample cell is also noted in Table 3.

TABLE 3

EFFECT OF OPTICAL COMPONENTS ON THE ACCURACY OF CHEMOMETRIC PREDICTIONS
(ALL ERRORS ARE IN WT %)

| Type of Optical Components | | | | | |
|---|---|---|---|---|---|
| Lamp | − | + | − | − | + |
| Switches | − | − | + | + | + |
| Sample Cell | − | − | − | − | + |
| Long Fiber | − | − | − | + | + |
| Fitted Variance (%) | | | | | |
| Spectral | 99.81 | 99.88 | 98.44 | 99.79 | 99.80 |
| n-Heptane | 99.34 | 99.58 | 99.31 | 99.13 | 99.53 |
| i-Octane | 99.95 | 99.83 | 99.91 | 99.81 | 99.96 |
| Toluene | 99.98 | 99.78 | 99.98 | 99.74 | 99.99 |
| p-Xylene | 99.90 | 99.93 | 99.87 | 99.91 | 99.92 |
| n-Decane | 99.77 | 99.83 | 99.80 | 99.67 | 99.81 |
| n-Alkanes | 99.99 | — | — | 99.97 | 99.99 |
| SEE Model (Wt %) | | | | | |
| n-Heptane | 0.52 | 0.42 | 0.54 | 0.60 | 0.45 |
| i-Octane | 0.14 | 0.26 | 0.20 | 0.27 | 0.13 |
| Toluene | 0.09 | 0.31 | 0.08 | 0.33 | 0.06 |
| p-Xylene | 0.12 | 0.10 | 0.13 | 0.11 | 0.11 |
| n-Decane | 0.47 | 0.40 | 0.43 | 0.55 | 0.42 |
| n-Alkanes | 0.09 | — | — | 0.15 | 0.09 |
| SEP (Wt %) | | | | | |
| n-Heptane | 1.10 | 0.75 | 1.33 | 0.96 | 0.88 |
| i-Octane | 0.30 | 0.41 | 0.42 | 0.34 | 0.27 |
| Toluene | 0.14 | 0.37 | 0.17 | 0.45 | 0.10 |
| p-Xylene | 0.12 | 0.15 | 0.17 | 0.14 | 0.14 |
| n-Decane | 0.91 | 0.57 | 1.08 | 0.82 | 0.73 |
| n-Alkanes | 0.16 | — | — | 0.19 | 0.16 |

(−) DENOTES TYPICAL LABORATORY OPTICAL COMPONENTS
(+) MODIFIED OR ADDITIONAL COMPONENTS

Table 3 illustrates that chemometric predictions obtained utilizing the field or manufacturing environment-enhanced optical components provided similar precision to the laboratory apparatus. Enhancing the spectrophotometer having high-efficiency fiber optic switches with the long fiber optic run between the second fiber optic switch and the spectrograph improved the accuracy of the predictions by acting as a mode scrambler, which improved precision in the spectral measurements. Adding the sample cell with fixed optics provided further prediction accuracy improvements.

EXAMPLE 3

The effects of uniform shifts in the wavelength axis (x-axis) of the intensity spectra on the accuracy of chemometric predictions was determined through software manipulations. Chemometric models were built and then the composition of samples were predicted after uniformly shifting the spectra. Shifts in the wavelength axis can be caused by mechanical vibrations or shocks or changes in the temperature of the spectrograph. The uniform shifts in wavelength axis were simulated through software by first assuming that the intensity was uniformly distributed across each pixel. Each pixel was about 0.25 nanometers wide, and the overtone band consisted of 400 pixels. The precision results of various shifts in the wavelength axis are illustrated in Table 4.

TABLE 4

EFFECT OF SHIFTING THE WAVELENGTH AXIS ON THE ACCURACY OF CHEMOMETRIC PREDICTIONS

| | Shift in Fraction of Pixel | | | | |
|---|---|---|---|---|---|
| | 0.01 | 0.03 | 0.10 | 0.30 | 1.00 |
| Bias (Wt %) | | | | | |
| n-Heptane | 0.00 | 0.16 | 0.49 | 1.64 | 4.91 | 16.36 |
| i-Octane | 0.00 | −0.02 | −0.07 | −0.23 | −0.70 | −2.35 |
| Toluene | 0.00 | 0.02 | 0.07 | 0.23 | 0.69 | 2.29 |
| p-Xylene | 0.00 | −0.03 | −0.08 | −0.28 | −0.85 | −2.81 |
| n-Decane | 0.00 | −0.13 | −0.40 | −1.34 | −4.03 | −13.46 |
| n-Alkanes | 0.00 | 0.03 | 0.09 | 0.29 | 0.87 | 2.91 |
| SEP (Wt %) | | | | | | |
| n-Heptane | 0.41 | 0.44 | 0.65 | 1.72 | 5.04 | 16.77 |
| i-Octane | 0.16 | 0.16 | 0.18 | 0.29 | 0.75 | 2.44 |
| Toluene | 0.15 | 0.15 | 0.17 | 0.28 | 0.72 | 2.35 |
| p-Xylene | 0.11 | 0.11 | 0.14 | 0.31 | 0.89 | 2.91 |
| n-Decane | 0.38 | 0.40 | 0.56 | 1.43 | 4.15 | 13.79 |
| n-Alkanes | 0.17 | 0.17 | 0.19 | 0.34 | 0.91 | 2.98 |

Table 4 illustrates that shifting the wavelength axis or spectrum by 0.03 pixels provides a noticeable increase in the error in prediction. Shifting the spectrum 0.10 pixels or 0.03 nanometers provides larger and more significant inflation in the error of prediction. Shifts of a full pixel in wavelength axis can provide chemometric predictions that may not be accurate enough to utilize for some process services.

The effects of uniform shifts in the wavelength axis caused by temperature variations in the spectrograph were determined by building a chemometric model at ambient temperature (around 70° F.) and heating the spectrograph to about 120° F. for sample prediction. In a separate experiment, predictions were made after the ambient temperature was decreased by 10° F. to about 60° F. The precision results from the ambient temperature induced wavelength axis shifts are illustrated in Table 5.

TABLE 5

EFFECT OF WAVELENGTH DRIFT ON THE ACCURACY OF CHEMOMETRIC PREDICTIONS. DRIFT WAS INDUCED BY HEATING THE SPECTOGRAPH AND BY CHANGES IN THE AMBIENT TEMPERATURE

| | Heat Spectrograph | | Reduce Ambient Temperature | |
|---|---|---|---|---|
| | Before | After | Before | After |
| Bias Wt % | | | | |
| n-Heptane | 0.04 | −5.72 | −0.32 | 1.34 |
| i-Octane | −0.03 | 0.09 | 0.06 | −0.36 |
| Toluene | −0.05 | 0.72 | −0.04 | 0.46 |
| p-Xylene | 0.08 | 0.17 | −0.06 | −0.26 |

TABLE 5-continued

EFFECT OF WAVELENGTH DRIFT ON THE ACCURACY
OF CHEMOMETRIC PREDICTIONS. DRIFT
WAS INDUCED BY HEATING THE SPECTOGRAPH AND
BY CHANGES IN THE AMBIENT TEMPERATURE

|  | Heat Spectrograph | | Reduce Ambient Temperature | |
| --- | --- | --- | --- | --- |
|  | Before | After | Before | After |
| n-Decane | −0.05 | 4.82 | 0.35 | −1.18 |
| n-Alkanes | −0.01 | −0.90 | 0.03 | 0.16 |
| SEP (Wt %) | | | | |
| N-Heptane | 0.24 | 6.70 | 0.50 | 1.55 |
| i-Octane | 0.10 | 0.56 | 0.12 | 0.41 |
| Toluene | 0.09 | 1.15 | 0.04 | 0.51 |
| p-Xylene | 0.15 | 0.66 | 0.09 | 0.31 |
| n-Decane | 0.20 | 5.70 | 0.52 | 1.40 |
| n-Alkanes | 0.04 | 1.05 | 0.04 | 0.18 |

Table 5 illustrates that changes in ambient temperature produce substantial errors in the precision of predictions. Extrapolating from Table 4, increasing the ambient temperature to 120° F. created a shift of about 0.4 pixels. The results of both the ambient temperature increase and decrease cases indicated that the wavelength axis can shift about 0.01 pixels per °F. change in ambient temperature. These tests further indicate that chemometric prediction accuracy can be gained by maintaining the spectrograph at a constant temperature or correcting for the ambient temperature changes mathematically. For example, a thermocouple can be installed in the spectrograph to measure the ambient temperature and utilize its signal to calculate and adjust for the shift in wavelength axis.

EXAMPLE 4

The effects of reducing the photometric precision of the spectrograph on the accuracy of chemometric predictions was similarly determined through software manipulations. Variables that affect photometric precision can include stray light in the spectrograph, the resolution of the intensity axis, noise, and non-linearity in the photo-electronics. Stray light can be caused by scattering from the fixed diffraction grating and was measured at about 1 part in 3000 for the spectrograph used. The effect of increasing stray light over this base level was simulated by adding a constant offset to the baseline of the intensity spectra. The effects of increasing stray light on photometric precision are illustrated in Table 6.

TABLE 6

THE EFFECT OF STRAY LIGHT
ON THE ACCURACY OF CHEMOMETRIC PREDICTIONS

| | Imposed Stray Light (Percent of Full-Scale Intensity) | | | | |
| --- | --- | --- | --- | --- | --- |
| | 0 | 0.1 | 0.3 | 1.0 | 3.0 |
| Bias Wt % | | | | | |
| n-Heptane | 0.00 | 0.11 | 0.34 | 1.13 | 3.39 |
| i-Octane | 0.00 | 0.06 | 0.18 | 0.61 | 1.90 |
| Toluene | 0.00 | −0.01 | −0.03 | −0.11 | −0.34 |
| p-Xylene | 0.00 | −0.06 | −0.19 | −0.64 | −1.98 |
| n-Decane | 0.00 | −0.10 | −0.30 | −0.99 | −2.97 |
| n-Alkanes | 0.00 | 0.01 | 0.04 | 0.14 | 0.42 |
| SEP (Wt %) | | | | | |
| Heptane | 0.41 | 0.42 | 0.53 | 1.23 | 3.51 |
| i-Octane | 0.16 | 0.17 | 0.25 | 0.67 | 2.03 |
| Toluene | 0.15 | 0.15 | 0.16 | 0.22 | 0.52 |
| p-Xylene | 0.11 | 0.13 | 0.22 | 0.67 | 2.04 |
| n-Decane | 0.38 | 0.39 | 0.49 | 1.09 | 3.10 |
| n-Alkanes | 0.17 | 0.17 | 0.18 | 0.30 | 0.78 |

Table 6 illustrates that stray light levels up to 0.1% of the full-scale intensity do not substantially affect the accuracy of chemometric predictions in this instance where the maximum absorbance level was about 0.5 units. In spectrophotometers having longer sample path lengths or analyzing substances having stronger absorbances, the effects of stray light can be more severe.

The effect of the resolution of the intensity axis (y-axis) on the accuracy of chemometric predictions, which generally depends on the signal-to-noise ratio of the photo-electronics, sampling time, and the resolution of the analog-to-digital converter, was simulated by rounding off the intensity measurement in the spectra used to build and test the chemometric models. The resolution of the intensity axis was given in bits, n, where the resolution is one part in $2^n$. The fewer the number of bits, the greater the round off error prior to modeling. The results of reduction in resolution of the intensity axis on prediction accuracy are illustrated in Table 7.

TABLE 7

EFFECT OF THE RESOLUTION OF
THE INTENSITY AXIS ON THE
ACCURACY OF CHEMOMETRIC PREDICTIONS

| | Resolution of Intensity Axis (bits) | | | | |
| --- | --- | --- | --- | --- | --- |
| | 15 | 12 | 10 | 9 | 8 |
| Fitted Variance (%) | | | | | |
| Spectral | 99.95 | 99.89 | 99.12 | 97.05 | 89.20 |
| n-Heptane | 99.61 | 99.63 | 99.13 | 98.09 | 95.94 |
| i-Octane | 99.93 | 99.93 | 99.91 | 99.90 | 99.80 |
| Toluene | 99.94 | 99.94 | 99.96 | 99.94 | 99.86 |
| p-Xylene | 99.41 | 99.90 | 99.89 | 99.89 | 99.62 |
| n-Decane | 99.84 | 99.84 | 99.70 | 99.39 | 98.58 |
| n-Alkanes | 99.96 | 99.97 | 99.96 | 99.95 | 99.93 |
| SEE Model (Wt %) | | | | | |
| n-Heptane | 0.41 | 0.40 | 0.61 | 0.90 | 1.30 |
| i-Octane | 0.16 | 0.16 | 0.19 | 0.20 | 0.28 |
| Toluene | 0.15 | 0.15 | 0.13 | 0.15 | 0.24 |
| p-Xylene | 0.11 | 0.12 | 0.12 | 0.12 | 0.23 |
| n-Decane | 0.39 | 0.38 | 0.53 | 0.73 | 1.25 |
| n-Alkanes | 0.17 | 0.17 | 0.18 | 0.20 | 0.23 |
| SEP (Wt %) | | | | | |
| n-Heptane | 0.86 | 0.78 | 0.87 | 1.43 | 4.45 |
| i-Octane | 0.34 | 0.33 | 0.34 | 0.36 | 0.84 |
| Toluene | 0.19 | 0.19 | 0.18 | 0.20 | 0.57 |
| p-Xylene | 0.11 | 0.12 | 0.14 | 0.29 | 0.85 |
| n-Decane | 0.65 | 0.61 | 0.80 | 1.26 | 3.82 |
| n-Alkanes | 0.28 | 0.26 | 0.20 | 0.24 | 0.69 |

Table 7 illustrates that a resolution of 10 bits, which corresponds to 0.0004 to 0.001 ABS, is suitable for intensity axis resolution in this instance where the peak absorbance was about 0.5. On the spectrophotometer utilized, this accuracy was obtained with one scan of the spectrum, which was completed in 20 msec. More resolution may be required for spectrophotometers having longer sample pathlengths or analyzing more strongly-absorbing materials.

The effect of spectral noise on the accuracy of chemometric predictions was determined by artificially imposing noise levels of different magnitudes onto the intensity spectra used for building and testing the chemometric models. The noise level at each point in the spectrum was selected using a random number generator operating within the constraints of the overall magnitude of the noise level desired. Noise can be produced in a spectrophotometer by the imprecise repositioning of the fiber optics in the switches and in the photoelectronics and the light source by electromagnetic interference and other electrical disturbances. The peak to peak noise level was described as a percent of the full-scale intensity range of the photodiodes. The results of increased noise on prediction accuracy are illustrated in Table 8.

TABLE 8

THE EFECT OF IMPOSED NOISE ON THE ACCURACY OF CHEMOMETRIC PREDICTIONS

| | Imposed Peak-to-Peak Noise Level (Percent of Full-Scale Intensity) | | | | |
|---|---|---|---|---|---|
| | 0 | 0.03 | 0.1 | 0.3 | 1.0 |
| Bias Wt % | | | | | |
| n-Heptane | 0.00 | −0.02 | 0.10 | −0.36 | 0.37 |
| i-Octane | 0.00 | 0.00 | 0.00 | 0.10 | −0.14 |
| Toluene | 0.00 | −0.00 | 0.01 | 0.00 | −0.06 |
| p-Xylene | 0.00 | 0.00 | −0.03 | −0.03 | 0.12 |
| n-Decane | 0.00 | 0.02 | −0.08 | −0.29 | −0.30 |
| n-Alkanes | 0.00 | 0.00 | 0.02 | −0.07 | 0.07 |
| SEP (Wt %) | | | | | |
| Heptane | 0.41 | 0.48 | 0.59 | 2.23 | 6.24 |
| i-Octane | 0.16 | 0.18 | 0.21 | 0.52 | 1.35 |
| Toluene | 0.15 | 0.16 | 0.16 | 0.34 | 0.91 |
| p-Xylene | 0.11 | 0.12 | 0.15 | 0.48 | 1.19 |
| n-Decane | 0.38 | 0.43 | 0.50 | 1.81 | 4.97 |
| n-Alkanes | 0.17 | 0.18 | 0.19 | 0.47 | 1.34 |

Table 8 illustrates that noise levels between 0.03% and 0.1% of full scale can effect the accuracy of the chemometric predictions. Over most of the test, the spectrophotometer of the present invention had a base noise level of 0.02% of full scale and was generally caused by the imprecise repositioning of the fiber optic cables in the switches.

EXAMPLE 5

The photometric linearity, or how accurately the light intensity signal was transformed into a proportional electrical signal, and the effects of linearity on the accuracy of chemometric predictions were determined for the apparatus of the present invention. The linearity was tested by measuring the spectra of mixtures of benzene and cyclohexane with known composition. This system was used because there is substantially no hydrogen bonding between molecules, the spectra of the two compounds have very little overlap, and both components are available in high purity (99+ wt %).

Since absorbance depends on the sample density, non-ideal mixing generally appears as a non-linearity in the absorbance and should be accounted for. The mixing of benzene and cyclohexane is non-ideal whereby the volume increase upon mixing can be approximated by:

$$\Delta V_{mix} = 0.03 \times W_b \times (1 - W_b)$$

where $W_b$ is the weight fraction of benzene in cyclohexane. The densities of mixtures of benzene and cyclohexane are illustrated in Table 9.

TABLE 9

DENSITIES OF MIXTURES OF BENZENE AND CYCLOHEXANE (g/cc @ 60° F.)

| Wt % Benzene | Measured Density | Ideal Density | $\Delta V_{mix}$ (%) |
|---|---|---|---|
| 0.00 | 0.7766 | — | 0.0 |
| 25.02 | 0.7918 | 0.7995 | 0.5 |
| 49.84 | 0.8170 | 0.8237 | 0.8 |
| 74.91 | 0.8453 | 0.9496 | 0.4 |
| 100.00 | 0.8772 | — | 0.0 |

Spectra of mixtures of benzene and cyclohexane, with known composition, were measured using spectrophotometers having two different silicon array detectors driven by different electronics (Spectrophotometers A and B). Spectrophotometer A utilized a Reticon S-Series photodiode array while Spectrophotometer B utilized a Reticon SB Series photodiode array. Chemometric models of composition were built for each spectrophotometer utilizing one latent variable and the SEE for each spectrophotometer and chemometric model determined. The SEP was also determined for a test set measured on Spectrophotometer A. The results of the evaluation of the absorbance linearity for Spectrophotometer A are illustrated in Table 10.

TABLE 10

EVALUATION OF THE ABSORBANCE LINEARITY OF SPECTROPHOTOMETER A USING SOLUTIONS OF BENZENE AND CYCLOHEXANE

| Wt % Benzene | Errors of Estimation (WT %) | Wt % Benzene | Errors of Prediction (WT %) |
|---|---|---|---|
| 0.0 | 0.34 | 0.05 | 0.31 |
| 10.3 | 0.35 | 1.04 | 0.27 |
| 20.4 | −0.10 | 2.02 | 0.25 |
| 30.4 | 0.06 | 5.03 | 0.17 |
| 39.6 | −0.48 | 10.04 | 0.06 |
| 50.0 | −0.41 | 19.99 | −0.22 |
| 59.8 | −0.17 | 50.03 | −0.35 |
| 69.7 | −0.26 | 100.00 | 0.69 |
| 79.6 | −0.06 | | |
| 89.7 | 0.16 | | |
| 100.0 | 0.55 | | |
| SEE | 0.33 | SEP | 0.36 |

Spectrophotometer B was further tested with and without isolating the spectrograph of Spectrophotometer B from vibrational effects. The operation of a nearby fume hood caused slight vibration in the laboratory bench. The results of the evaluation for Spectrophotometer B are illustrated in Table 11.

TABLE 11

EVALUATION OF THE ABSORBANCE LINEARITY OF SPECTROPHOTOMETER B USING SOLUTIONS OF BENZENE AND CYCLOHEXANE

| | Errors of Estimation (Wt %) | |
|---|---|---|
| Wt % Benzene | Without Vibration Isolation | With Vibration Isolation |
| 0.0 | 0.21 | 0.18 |
| 10.6 | 0.32 | 0.30 |
| 20.2 | 0.02 | 0.04 |
| 29.5 | −0.12 | −0.16 |
| 40.0 | −0.16 | −0.18 |
| 50.3 | −0.20 | −0.18 |
| 59.8 | −0.50 | −0.28 |
| 68.6 | −0.11 | −0.17 |
| 80.1 | 0.03 | 0.01 |
| 91.0 | −0.04 | −0.03 |
| 100.0 | 0.56 | 0.48 |
| SEE | 0.30 | 0.25 |

Tables 10 and 11 illustrate that the observed non-linearities of −0.7 wt % to −0.9 wt %, determined as the average SEE of the 0.0 wt % benzene and 100.0 wt % benzene cases less the SEE of the 50 wt % benzene case, are very close to those expected from the non-ideal mixing of the constituents. The apparent non-linearities of the photo-response for both Spectrophotometers A and B were less than 0.1 wt % at 50 wt % benzene, or 0.2%. Since the SEEs were similar for the cases where vibration was and was not isolated, Spectrophotometer B was not sensitive to vibrations. In this instance, the maximum absorbance was about 0.7 units.

In instances where the maximum absorbance is lower, the non-linearity may be less severe.

Spectrophotometer A was further tested for photometric linearity, that is, linearity in the intensity measurements, by building chemometric models for benzene, changing the photometric range, and predicting the compositions of unknowns. The photometric range was varied by changing the intensity of the light source, the sampling rate, and by inserting a 700 ft. long run of 200 micron fiber optic cable into the optical path. The SEPs for each case were determined with and without respect to the control samples used to uniquely determine the errors caused by photometric non-linearity. The results of the evaluation of photometric linearity are illustrated in Table 12.

TABLE 12

TEST OF PHOTOMETRIC LINEARITY BY VARYING THE SOURCE INTENSITY AND SCAN RATE, AND BY INSERTING 200 m OF FIBER INTO THE OPTICAL PATH (ERRORS OF PREDICTION ARE FOR WT % BENZENE IN CYCLOHEXANE)

| | | | | | | | | |
|---|---|---|---|---|---|---|---|---|
| Source Intensity (% Full-Scale) | 80 | 60 | 40 | 20 | 80 | 80 | 80 | 80* |
| Sampling Rate (Spectra/Sec) | 25 | 25 | 25 | 25 | 25 | 50 | 100 | 25 |
| Model w/1 Latent Vector | | | | | | | | |
| SEP | 0.51 | 0.51 | 0.50 | 0.52 | 0.52 | 0.53 | 0.54 | 0.59 |
| SEP wrt Control | 0.00 | 0.07 | 0.13 | 0.21 | 0.00 | 0.06 | 0.05 | 0.20 |
| Model w/2 Latent Vector | | | | | | | | |
| SEP | 0.32 | 0.31 | 0.33 | 0.36 | 0.30 | 0.34 | 0.33 | 0.38 |
| SEP wrt Control | 0.00 | 0.07 | 0.13 | 0.21 | 0.00 | 0.06 | 0.05 | 0.23 |

*200 m of fiber optic inserted into optical path

Table 12 illustrates that when the photometric range was reduced up to four-fold by reducing the source intensity or sampling rate, the predictions of concentration were accurate to 0.2 wt % with respect to the controls. When the spectral range was attenuated non-uniformly by inserting the long run of fiber optic cable, similar accuracy was obtained. The results of the photometric linearity tests indicated that the photometric response of the apparatus of the present invention is linear to better than 0.2% of full scale. For best results, the scan rate of the photoarray detector was increased to maintain the maximum intensity on any of the detectors below 85% of the saturation value.

EXAMPLE 6

The effect of sampling time and sampling rate on the accuracy of chemometric predictions was determined for the apparatus of the present invention. A chemometric model was built using spectra averaged over 1000 scans, then the spectra of unknowns were measured by averaging a variable number of scans. The effect of varying sampling time was varied by changing the number of scans from 1 to 1000 scans and then determining the Bias and SEP. The results are illustrated in Table 13.

TABLE 13

EFFECT OF SAMPLING TIME ON THE ACCURACY OF CHEMOMETRIC PREDICTIONS

| | # Scans at 50 Spectra/Sec | | | |
|---|---|---|---|---|
| | 1000 | 100 | 10 | 1 |
| Bias Wt % | | | | |
| n-Heptane | 0.43 | 0.30 | 0.20 | 0.04 |
| i-Octane | −0.01 | −0.07 | −0.03 | 0.02 |
| Toluene | −0.09 | −0.04 | −0.19 | −0.02 |
| p-Xylene | 0.05 | −0.04 | 0.01 | −0.05 |
| n-Decane | −0.40 | −0.18 | −0.14 | −0.02 |
| n-Alkanes | 0.03 | 0.12 | −0.06 | 0.03 |

TABLE 13-continued

EFFECT OF SAMPLING TIME ON THE ACCURACY OF CHEMOMETRIC PREDICTIONS

| | # Scans at 50 Spectra/Sec | | | |
|---|---|---|---|---|
| | 1000 | 100 | 10 | 1 |
| SEP (Wt %) | | | | |
| Heptane | 0.67 | 0.54 | 0.37 | 0.60 |
| I-Octane | 0.21 | 0.32 | 0.26 | 0.31 |
| Toluene | 0.12 | 0.20 | 0.42 | 0.15 |
| p-Xylene | 0.13 | 0.14 | 0.12 | 0.15 |
| n-Decane | 0.60 | 0.46 | 0.37 | 0.46 |
| n-Alkanes | 0.17 | 0.24 | 0.15 | 0.21 |

Table 13 illustrates that predictions from a single scan were generally as accurate as those obtained by averaging 1000 scans. This was expected from previous results because the noise in the spectra is random and is about 0.1% of the intensity scale for a single scan. As was shown in Table 7, this level of random noise has minimal effect on the accuracy of the chemometric predictions.

EXAMPLE 7

The effects of changes in the optical path on the accuracy of chemometric predictions were determined by making changes in the optical path both inside and outside the high-efficiency fiber optic switches. The fiber optic path was first changed by remaking connections in the optical path that was common to the sample and reference channels. The test was performed on a spectrophotometer without an attenuator or a mode scrambler. The results of changing the optical path as described above are illustrated in Table 14.

TABLE 14

EFFECT OF CHANGES IN THE OPTICAL PATH COMMON TO THE SAMPLE AND REFERENCE CHANNELS ON THE ACCURACY OF CHEMOMETRIC PREDICTIONS

| | Control | Remake Connection Outside Switches |
|---|---|---|
| Bias (wt %) | | |
| n-Heptane | 0 | −0.38 |
| i-Octane | 0.01 | −0.21 |
| Toluene | 0 | −0.15 |
| p-Xylene | −0.07 | 0.50 |
| n-Decane | 0.06 | 0.23 |
| n-Alkanes | 0.06 | −0.15 |
| SEP (wt %) | | |
| n-Heptane | 0.52 | 0.64 |
| i-Octane | 0.10 | 0.23 |
| Toluene | 0.11 | 0.18 |
| p-Xylene | 0.07 | 0.57 |
| n-Decane | 0.56 | 0.53 |

TABLE 14-continued

EFFECT OF CHANGES IN THE OPTICAL PATH
COMMON TO THE SAMPLE AND REFERENCE
CHANNELS ON THE ACCURACY OF
CHEMOMETRIC PREDICTIONS

|  | Control | Remake Connection Outside Switches |
|---|---|---|
| n-Alkanes | 0.06 | 0.20 |

Table 14 illustrates that remaking a fiber optic connection outside the fiber optic switches had little effect on prediction accuracy. This is because measuring the intensity spectra for the sample and reference channels compensates for aberrations in the optics that are common to the two channels. Altering the optics in the path that is unique to the sample or reference channel has larger effects on prediction accuracy.

The fiber optic between the two high-efficiency fiber optic switches was then changed by moving the fiber optic cable in the sample channel, swapping fiber optic switches, and inserting a new sample cell. The apparent absorbance spectrum was then adjusted for the changes in the background spectrum or sample path length. The relative path length for the two sample cells was determined by measuring the apparent absorbance of benzene, substracting the background spectrum, and ratioing the difference between cells. These tests were also performed on a spectrophotometer without an attenuator or a mode scrambler. The results of changing the optical path as described above are illustrated in Table 15.

sample cell with carbon tetrachloride. The same spectra for each of the 29 samples were used for modeling and prediction, except that the background correction was applied to each spectrum before modeling the composition, but not applied when the spectra were used to predict composition. The results are illustrated in Table 16.

TABLE 16

EFFECT OF NEGLECTING THE BACKGROUND
CORRECTION ON THE ACCURACY OF CHEMOMETRIC
PREDICTIONS

| Constituent | Bias (wt %) | SEP (wt %) |
|---|---|---|
| n-Heptane | −0.47 | 0.63 |
| i-Octane | 0.16 | 0.23 |
| Toluene | 0.37 | 0.41 |
| p-Xylene | −0.21 | 0.24 |
| n-Decane | 0.14 | 0.41 |
| n-Alkanes | −0.33 | 0.38 |

Table 16 illustrates that ignoring the background correction in a spectrophotometer having an attenuator and a mode scrambler provided reasonable accuracy. The biases in the prediction of concentration averaged about 0.3 wt %.

EXAMPLE 8

The effect of drift in the background spectrum, which can be caused by inconsistency or non-repeatability in the high-efficiency fiber optic switches, on the accuracy of chemometric predictions was determined for the spectrophotometer of the present invention.

TABLE 15

EFFECT OF CHANGING THE OPTICAL PATH BETWEEN THE SAMPLE AND REFERENCE
CHANNELS ON THE ACCURACY OF CHEMOMETRIC PREDICTIONS

|  | MOVE FIBER OPTIC | | | SWAP FIBER SWITCH | | | SWAP SAMPLE CELL | | |
|---|---|---|---|---|---|---|---|---|---|
|  | INITIAL | AFTER CHANGE | AFTER CORRECTION | INITIAL | AFTER CHANGE | AFTER CORRECTION | INITIAL | AFTER CHANGE | AFTER CORRECTION |
| BIAS (WT %) | | | | | | | | | |
| n-Heptane | 0.07 | 0.74 | −0.08 | 0.04 | 8.11 | −0.33 | 0.04 | −2.18 | −0.67 |
| i-Octane | −0.04 | −0.13 | 0.09 | −0.03 | −0.24 | 0.17 | −0.03 | 0.07 | 0.36 |
| Toluene | 0.03 | 0.07 | −0.16 | −0.05 | −0.11 | 0.22 | −0.05 | 0.00 | 0.01 |
| p-Xylene | 0.01 | −0.30 | 0.06 | 0.08 | 0.40 | −0.38 | 0.08 | 0.02 | −0.49 |
| n-Decane | −0.12 | −0.39 | 0.19 | −0.05 | −8.16 | 0.37 | −0.05 | 2.14 | 0.84 |
| n-Alkanes | −0.05 | 0.35 | 0.11 | 0.01 | −0.04 | 0.04 | 0.01 | −0.04 | 0.18 |
| SEP (wt %): | | | | | | | | | |
| n-Heptane | 0.55 | 0.96 | 0.54 | 0.24 | 9.11 | 0.98 | 0.24 | 2.24 | 0.88 |
| i-Octane | 0.46 | 0.46 | 0.44 | 0.10 | 0.30 | 0.22 | 0.10 | 0.20 | 0.42 |
| Toluene | 0.42 | 0.33 | 0.37 | 0.09 | 0.12 | 0.24 | 0.09 | 0.14 | 0.08 |
| p-Xylene | 0.22 | 0.38 | 0.20 | 0.15 | 0.46 | 0.43 | 0.15 | 0.12 | 0.56 |
| n-Decane | 0.67 | 0.76 | 0.67 | 0.20 | 9.16 | 0.84 | 0.20 | 2.19 | 1.02 |
| n-Alkanes | 0.31 | 0.52 | 0.36 | 0.04 | 0.19 | 0.20 | 0.04 | 0.05 | 0.22 |

Table 15 illustrates that moving the fiber optics between the high-efficiency fiber optic switches and swapping a fiber high-efficiency optic switch or sample cell with a similar type, produced sizeable prediction errors. Where the fiber optic was moved, adjusting for changes in the background spectrum nearly eliminated the bias in the measurement. Where the high-efficiency fiber optic switches and sample cells were swapped, the adjustment for changes in the background spectrum reduced the bias significantly, but not entirely.

The addition of an attenuator and mode scrambler to the spectrophotometer made the predictions less sensitive to changes in the background spectrum. In this Example, the attenuator had two plano-convex lenses for collimating the light between the launching and receiving fiber optic cables in the reference channel. The background spectrum was measured by filling the Light launched from a fiber optic cable onto a flat surface generally images as a fairly homogeneous spot. Light launched through a switch generally images as a small, intense central spot surrounded by a more diffuse spot. Upon cycling, the spot can move slightly. When the switch launched directly into the spectrograph, this particular movement resulted in an apparent shift in the wavelength axis and errors in chemometric predictions. This effect was reduced by inserting a mode scrambler between the switch and the spectrograph. The mode scrambler made images from the switch more uniform both in spot size and in the radial distribution of light in the spot.

The mode scrambler used in this Example was made by wrapping the fiber optic cable around two half inch diameter spools in a figure eight pattern, using four complete repetitions of the figure eight pattern. The drift, for purposes of this Example, is given by the switching noise, which is defined as the maximum difference in the first-derivative spectra before and after 100,000 switching cycles at 20 Hz. For the control case, the sample and reference spectra were obtained using the same channel without cycling the switch. The typical photometric range in the first-derivative spectrum of a sample was 0.02 dABS, about 400 times greater than the noise given by the control. The results of mode scrambling, as described above are illustrated in Table 17.

TABLE 17

THE EFFECT OF MODE SCRAMBLING ON THE SWITCHING NOISE, WHICH IS RELATED TO DRIFT IN THE BACKGROUND SPECTRUM

|  | Peak-to-Peak Switching Noise (dABS × $10^4$) |
|---|---|
| Control, no switching | 0.5 |
| No mode scrambler | 5 |
| Mode scrambler | 0.9 |
| Two mode scrambler in series | 1 |
| Mode scrambler in series with 700 ft of fiber optic cable | 0.7 |
| Mode scrambler with cladding mode filter | 2 |

Table 17 illustrates that in the absence of a mode scrambler, the noise level after 100,000 switching cycles was 10 times larger than the control or the inherent noise level of the instrument with the high-efficiency fiber optic switches held stationary. When the mode scrambler was used, the noise was only twice that of the control. Attempts to decrease switching noise by placing two mode scramblers in series and placing a mode scrambler in series with a long run of fiber optic cable provided minimal benefit. Similarly, a mode scrambler that stripped out cladding modes corresponding to light which propagates in the cladding rather than the core of the fiber optics, resulted in a slightly smaller, sharper spot, but did not reduce the switching noise further.

The noise from cycling the high-efficiency fiber optic switches was compared with the noise caused by bending the fiber optic cable and by misaligning the fibers in the fiber optic switch. Either of these effects can cause switching noise. The noise was further measured for switches made from fluorocarbon clad fibers (FCS) and glass clad fibers (GCS), and with and without a mode scrambler. For the control, the switches were cycled 100,000 times. For the other tests, the fiber optic leading to the sample cell was bent on a three-inch radius, and the fiber was misaligned by shimming the stop with a thin plastic sheet, which reduced the overall light transmission through the switch by 10-20%. The mode scramblers used in this Example were made from FCS fiber wrapped around two half-inch diameter spools in a figure-eight pattern, using four complete repetitions of the figure-eight pattern. The results of the comparison are illustrated in Table 18.

TABLE 18

EFFECTS OF FIBER TYPE AND MODE SCRAMBLING ON THE NOISE CAUSED BY CYCLING THE FIBER SWITCHES, BENDING THE FIBER OPTICS AND MISALIGNING FIBERS IN THE SWITCH

| | Noise in dABS × $10^4$ | | | |
|---|---|---|---|---|
| | FCS Fiber without Mode Scrambler | FCS Fiber with Mode Scrambler | GCS Fiber without Mode Scrambler | GCS Fiber with Mode Scrambler |
| 100,000 switching cycles | 3 | 0.8 | 2.5 | 1.7 |
| Bending the fiber | 2.5 | 1.5 | 4 | 1.5 |
| Misaligning the fiber | 3 | 1.2 | 8 | 5 |

Table 18 illustrates that it is unclear as to whether the switching noise was caused by bending or misalignment of the fiber optics. However, the mode scrambler reduced noise from all three sources and is suitable and beneficial for use with spectrophotometers having fiber optics. The switches made with FCS fiber optic cable were less noisy than those made with GCS fiber optic cable. It is believed that this is related to the fact that the light output changed much more gradually with the angle of propagation in the FCS fiber. The FCS fiber optic cable is generally preferred over the GCS fiber optic cable for use in the high-efficiency fiber optic switches because it is less noisy. Adversely, however, the FCS fiber optic cable also absorbed more light than the GCS fiber optic cable, so the GCS fiber is preferred in long runs of fiber optic cable. When a mode scrambler was used, cycling the switches caused little error in the chemometric predictions.

The effect of correcting for the change in the background specturum was measured. Chemometric models were tested before and after about 2,000,000 cycles, which gave a switching noise of 0.0002 dABS. The change in the background spectrum was also measured and the switching noise was removed by correcting for the drift in the background spectrum. The results of correcting for the background spectrum are illustrated in Table 19.

TABLE 19

EFFECT OF CYCLING THE FIBER OPTIC SWITCHES ON THE ACCURACY OF CHEMOMETRIC PREDITIONS

| | CASE 1 | | | CASE 2 | | | CASE 3 | |
|---|---|---|---|---|---|---|---|---|
| | INITIAL | AFTER CYCLING | AFTER CORRECTION | INITIAL | AFTER CYCLING | AFTER CORRECTION | INITIAL | AFTER CYCLING |
| BIAS (wt %) | | | | | | | | |
| n-Heptane | −0.04 | −0.75 | — | −0.15 | 1.60 | 1.49 | −0.32 | 1.22 |
| i-Octane | −0.03 | 0.12 | — | −0.04 | −0.17 | −0.18 | 0.06 | −0.37 |
| Toluene | −0.04 | −0.18 | — | 0.02 | 0.25 | 0.21 | −0.04 | 0.30 |
| p-Xylene | 0.14 | 0.13 | — | 0.02 | −0.29 | −1.32 | −0.06 | −0.09 |
| n-Decane | −0.02 | 0.68 | — | 0.16 | −1.38 | −1.19 | 0.35 | −1.05 |
| n-Alkanes | −0.07 | −0.06 | — | 0.01 | 0.22 | 0.30 | 0.03 | 0.17 |
| SEP (wt %): | | | | | | | | |
| n-Heptane | 1.14 | 0.89 | — | 0.51 | 1.86 | 1.73 | 0.50 | 1.43 |
| i-Octane | 0.17 | 0.18 | — | 0.14 | 0.25 | 0.26 | 0.12 | 0.44 |
| Toluene | 0.18 | 0.22 | — | 0.08 | 0.29 | 0.26 | 0.04 | 0.34 |
| p-Xylene | 0.21 | 0.15 | — | 0.05 | 0.35 | 0.38 | 0.09 | 0.19 |

TABLE 19-continued
EFFECT OF CYCLING THE FIBER OPTIC SWITCHES ON THE ACCURACY OF CHEMOMETRIC PREDITIONS

| | | | | | | | | |
|---|---|---|---|---|---|---|---|---|
| n-Decane | 0.94 | 0.80 | — | 0.38 | 1.59 | 1.39 | 0.52 | 1.26 |
| n-Alkanes | 0.22 | 0.10 | — | 0.13 | 0.29 | 0.37 | 0.04 | 0.20 |

| | CASE 3 | CASE 4 | | |
|---|---|---|---|---|
| | AFTER CORRECTION | INITIAL | AFTER CYCLING | AFTER CORRECTION |
| BIAS (wt %) | | | | |
| n-Heptane | 1.70 | 0.07 | −0.26 | 0.21 |
| i-Octane | −0.30 | −0.04 | 0.09 | 0.05 |
| Toluene | 0.26 | 0.03 | −0.31 | −0.19 |
| p-Xylene | −0.14 | −0.01 | 0.13 | −0.02 |
| n-Decane | −1.52 | −0.12 | 0.34 | 0.35 |
| n-Alkanes | 0.18 | −0.05 | 0.07 | 0.14 |
| SEP (wt %): | | | | |
| n-Heptane | 1.96 | 0.55 | 0.56 | 0.54 |
| i-Octane | 0.37 | 0.46 | 0.55 | 0.55 |
| Toluene | 0.29 | 0.42 | 0.55 | 0.49 |
| p-Xylene | 0.22 | 0.22 | 0.28 | 0.24 |
| n-Decane | 1.77 | 0.67 | 0.81 | 0.82 |
| n-Alkanes | 0.21 | 0.31 | 0.42 | 0.44 |

Table 19 illustrates that the switching noise, which was removed by correcting for the drift in the background spectrum, caused relatively little bias in the predictions. Most of the errors could be attributed to drift in the wavelength axis caused by thermally induced movements between optical components of the spectrograph, rather than cycling of the high-efficiency fiber optic switches. For the last replicate in Table 19, where an effort was made to minimize the wavelength drift, the SEPs for each constituent differed by about 0.1 wt % before and after cycling.

EXAMPLE 9

The effect of increasing and decreasing sample temperature, on the accuracy of chemometric predictions was determined for the spectrophotometer of the present invention. The temperature dependence of absorbance was measured for toluene, iso-octane, cyclohexane, carbon tetrachloride, and reformate. The optics of the sample cell were mounted in a housing designed for an in-line probe. The probe was placed in a test stand where the sample temperature could be increased at constant pressure. The change in absorbance, averaged over all wavelengths, was calculated by linear regression at each temperature. For each sample, the apparent thermal expansion was determined from the change in absorbance.

For carbon tetrachloride, the control, the maximum difference in the spectra between 75° F. and 186° F. was 0.0002 dABS, which was substantially caused by switching noise. The apparent coefficients of expansion for isooctane, toluene, and reformate (0.05%/°F., 0.06%/°F., and 0.06%/°F.) were close to the literature values of 0.06%/°F. The value for cyclohexane was much less than expected (0.04%/°F. as compared to 0.07%/°F.), and this was attributed to cyclohexane undergoing conformational changes in this temperature range which may have caused the unexpected result.

The composition of mixtures of benzene and isooctane were predicted over a temperature range of from about 75° F. to about 187° F. and predictions were made with and without correcting for thermal expansion. The chemometric model was built at 75° F. and a coefficient of expansion of 0.06%/°F. was used. The SEPs were calculated for each comparison test. The results of these comparison tests are illustrated in Table 20.

TABLE 20
HOW TEMPERATURE AFFECTS THE PREDICTION OF WT % BENZENE IN ISO-OCTANE

| MODEL WITH 2 LATENT VECTORS | | ERRORS OF PREDICTION (Wt %) FOR 60.5% BENZENE SOLN. | | | ERRORS OF PREDICTION (Wt %) FOR 89.7% BENZENE SOLN. | | |
|---|---|---|---|---|---|---|---|
| Wt % BENZENE | MODEL ERROR (Wt %) | °F. | RAW | CORRECTED | °F. | RAW | CORRECTED |
| 0.0 | 1.7 | 76 | 1.0 | 1.0 | 75 | 0.3 | 0.3 |
| 10.1 | −1.3 | 84 | 1.0 | 1.0 | 84 | −0.8 | −0.6 |
| 21.8 | −0.8 | 95 | 0.9 | 1.0 | 95 | −0.8 | −0.4 |
| 30.7 | −0.6 | 105 | 0.8 | 0.8 | 105 | −1.0 | −0.4 |
| 41.2 | 0.7 | 118 | 0.7 | 0.8 | 116 | −0.9 | −0.1 |
| 51.3 | −0.4 | 126 | 0.7 | 0.8 | 124 | −0.8 | 0.2 |
| 60.5 | 0.5 | 137 | 0.6 | 0.7 | 136 | −0.8 | 0.3 |
| 69.7 | 0.6 | 148 | 0.6 | 0.6 | 144 | −0.9 | 0.4 |
| 80.9 | 0.1 | 158 | 0.5 | 0.6 | 155 | −0.8 | 0.5 |
| 89.7 | 0.9 | 164 | 0.5 | 0.5 | 166 | −0.9 | 0.6 |
| 100.00 | 1.0 | 174 | 0.4 | 0.5 | 177 | −1.0 | 0.7 |
| 100.00 | −1.9 | 186 | 0.3 | 0.5 | 187 | −1.2 | 0.7 |
| Bias | — | | 0.7 | 0.7 | | −0.8 | 0.2 |
| Std. Dev. | 1.1 | | 0.2 | 0.2 | | 0.4 | 0.4 |

Table 20 illustrates that the corrected and uncorrected SEPs were within the modeling error (SEE) of 1.1 wt %. However, the corrected predictions had less bias for the high benzene concentration. Although the effect of sample temperature was small, the error in the predictions decreased when a correction was made for thermal expansion. Changing the sample temperature introduces artifacts or structures into the spectra that are difficult to compensate for. A chemometric model can be built over a broad range of temperature and composition, but a large number of samples would be required. Controlling the sample temperature within a range of 40° F. and more preferably 30° F. for compounds without hydrogen bonding would limit the appearance of artifacts, and correcting for thermal expansion would provide first order compensation for the effects of temperature.

EXAMPLE 10

The effects of sample flowrate on the accuracy of chemometric predictions were determined by comparing the spectra of a reformate stream at flowrates of 0 ccm and 500 ccm. At 500 ccm, the transmission of light through the sample was attenuated by 80% to 90%. However the first derivative spectra of absorbance appeared substantially similar for the two flowrates. Flow through the sample probe was not fully developed into an equilibrium velocity distribution in the opening of the sample cell, but the maximum velocity at 500 ccm was 0.1 to about 1.0 ft/sec. The attenuation of the light transmission through the sample was caused by scattering from either gas bubbles or density fluctuations in the liquid. Flowrate is unlikely to substantially effect chemometric prediction accuracy if the process is sampled though a slipstream and the maximum velocity in the sample cell is maintained below 1 ft/sec and preferably below 0.1 ft/sec. However, in order to transmit enough light through the sample, it may be necessary to reduce the liquid velocity through an in-line probe to similar levels.

That which is claimed is:

1. An apparatus for obtaining spectral information and quantifying the physical properties of a sample comprising:
   a light source for providing light;
   a high-efficiency fiber optic switch means, in communication with said light source through a single fiber optic strand, said high-efficiency fiber optic switch means directing said light alternatively along at least two channels, said channels comprising at least one reference channel and at least one sample channel;
   a sampling means in communication with said sample channel for providing an interface between said light and said sample;
   a mode scrambler;
   a fiber optic means selected from the group consisting of a high-efficiency fiber optic switch and an optical coupler, in communication with said sample channels and said reference channels for directing said light alternatively from said reference and sample channels to said mode scrambler;
   a wavelength discrimination device for separating said light into component wavelengths and providing spectral information for the determination of the physical properties of said sample.

2. The apparatus of claim 1 wherein said light source is a polychromatic light source.

3. The apparatus of claim 2 wherein said polychromatic light source is a tungsten-halogen lamp.

4. The apparatus of claim 1 wherein said fiber optic means is a high-efficiency fiber optic switch and said high-efficiency fiber optic switch means and said fiber optic means consisting of a high-efficiency fiber optic switch have mechanical motion mechanisms.

5. The apparatus of claim 4 wherein said mechanical motion mechanisms are latching type mechanical motion switches.

6. The apparatus of claim 1 wherein said high-efficiency fiber optic switch directs said light to and from one reference channel and at least one sample channel.

7. The apparatus of claim 1 wherein said mode scrambler comprises a long run of fiber optic cable ranging in length from about 100 feet to about 5000 feet.

8. The apparatus of claim 1 wherein said spectral information is limited to wavelengths in the range of from about 800 nanometers to about 1100 nanometers.

9. The apparatus of claim 1 wherein said wavelength discrimination device comprises a spectrograph, said spectrograph comprises a diffraction grating and a photodiode array detector, and said photodiode array detector has a spatial resolution of at least 1 pixel per nanometer.

10. The apparatus of claim 1 wherein said wavelength discrimination device comprises a spectrograph, said spectrograph comprises a diffraction grating and a photodiode array detector, and said photodiode array detector has a wavelength resolution of better than 4 nanometers.

11. An apparatus for obtaining spectral information and quantifying the physical properties of materials comprising:
    a polychromatic light source for providing light;
    a first high-efficiency fiber optic switch means, in communication with said polychromatic light source through a single fiber optic strand, said high-efficiency fiber optic switch means directing said polychromatic light alternatively along at least two channels, said channels comprising at least one reference channel and at least one sample channel;
    a sampling means in communication with said sample channel for providing an interface between said polychromatic light and said sample;
    an attenuation means along said reference channel for balancing the polychromatic light transmission between the sample and reference channels;
    a mode scrambler;
    a second high-efficiency fiber optic switch means, in communication with said sample channels and said reference channels for directing said polychromatic light alternatively from said reference and sample channels to said mode scrambler;
    a spectrograph for diffracting said polychromatic light into component wavelengths and providing spectral information for the determination of the physical properties of said sample.

12. The apparatus of claim 11 wherein said polychromatic light source is a tungsten-halogen lamp.

13. The apparatus of claim 11 wherein said first and second high-efficiency fiber optic switches are mechanical motion switches and direct said polychromatic light to and from one reference channel and at least one sample channel.

14. The apparatus of claim 11 wherein the fiber optics used in said high-efficiency fiber optic switches are externally cladded and said external cladding material comprises fluorocarbon.

15. The apparatus of claim 11 wherein said mode scrambler comprises a long run of fiber optic cable ranging in length from about 100 feet to about 5000 feet.

16. The apparatus of claim 11 wherein said spectrograph comprises a diffraction grating and a photodiode array detector and said photodiode array detector has a spatial resolution of at least 2 pixels per nanometer.

17. The apparatus of claim 11 wherein said spectrograph comprises a diffraction grating and a photodiode array detector and said photodiode array detector has a wavelength resolution of better than 4 nanometers.

18. The apparatus of claim 11 wherein said attenuation means comprises at least one member selected from the group consisting of one or more lenses, fiber optic cable, and fiber optic cable connecting devices.

19. The apparatus of claim 18 wherein said attenuation means comprises two plano convex lenses in series.

20. The apparatus of claim 11 wherein the optical elements of said spectrograph are mounted on temperature expansion resistance materials, said materials comprising at least one member selected from the group consisting of carbon fibers in an epoxy matrix and graphite fibers in an epoxy matrix.

21. The apparatus of claim 11 wherein the optical elements of said spectrograph are mounted on temperature expansion resistance materials, said materials comprising at least one carbon fiber in an epoxy matrix.

22. An apparatus for obtaining spectral information and quantifying the physical properties of materials comprising:
   a polychromatic light source for providing polychromatic light;
   a first high-efficiency fiber optic switch means, in communication with said polychromatic light source, said high-efficiency fiber optic switch means directing said polychromatic light alternatively along at least two channels, said channels comprising one reference channel and at least one sample channel;
   a sample cell, in communication with said sample channel for providing an interface between said polychromatic light and said sample, said sample cell comprising a reflection device for passing said polychromatic light through said sample at least once;
   an attenuation means along said reference path for balancing the polychromatic light transmission between the sample and reference channels;
   a mode scrambler;
   a second high-efficiency fiber optic switch means, in communication with said sample channels and said reference channel for directing said polychromatic light alternatively from said reference and sample channels to said mode scrambler;
   a spectrograph comprising a fixed diffraction grating, a photodiode array detector, and optical elements for imaging polychromatic light from said mode scrambler onto said diffraction grating and onto said photodiode array detector, for diffracting said polychromatic light into component wavelengths and providing spectral information for the determination of the physical properties of said sample.

23. The apparatus of claim 22 wherein said polychromatic light source is a tungsten-halogen lamp.

24. The apparatus of claim 22 wherein said first and second high-efficiency fiber optic switches are latching type mechanical motion switches.

25. The apparatus of claim 22 wherein said high-efficiency fiber optic switches comprise a manifold and a multi-plexer device for directing light to and from one reference channel and at least two sample channels.

26. The apparatus of claim 22 wherein spectral information is limited to wavelengths in the range of from about 850 nanometers to about 1000 nanometers.

27. The apparatus of claim 22 wherein said mode scrambler comprises a long run of fiber optic cable ranging in length from about 200 feet to about 2000 feet.

28. The apparatus of claim 22 wherein said photodiode array detector has a spatial resolution of at least 2 pixels per nanometer.

29. The apparatus of claim 22 wherein said photodiode array detector has a wavelength resolution of better than 2 nanometers.

30. The apparatus of claim 22 wherein said attenuation means comprises two plano convex lenses in series.

31. The apparatus of claim 22 wherein said sample cell reflection device reflects said polychromatic light at least 3 times and passes said polychromatic light through said sample stream at least twice.

32. The apparatus of claim 22 wherein said sample cell is inserted into the sample source, said sample source comprising at least one member selected from the group consisting of a pipeline and a vessel.

33. The apparatus of claim 22 wherein said sample cell is positioned at a location away from the sample source and said sample is directed to said sample cell through a slip-stream.

34. The apparatus of claim 22 wherein the optical elements of said spectrograph are mounted on temperature expansion resistance materials, said materials comprising at least one member selected from the group consisting of carbon fibers in an epoxy matrix and graphite fibers in an epoxy matrix.

35. The apparatus of claim 22 wherein the optical elements of said spectrograph are mounted on materials comprising at least one carbon fiber in an epoxy matrix.

* * * * *